US010639287B2

(12) United States Patent
Delahodde et al.

(10) Patent No.: US 10,639,287 B2
(45) Date of Patent: May 5, 2020

(54) COMPOUNDS FOR THE TREATMENT OF MITOCHONDRIAL DISEASES

(71) Applicants: UNIVERSITE PARIS-SUD, Orsay (FR); CENTRE NATIONAL DE LA RECHERCHE SCIENTIFIQUE, Paris (FR); UNIVERSITE D'ANGERS, Angers (FR); CENTRE HOSPITALIER UNIVERSITAIRE D'ANGERS, Angers (FR)

(72) Inventors: Agnes Delahodde, Verrieres le Buisson (FR); Laras Ajeng Pitayu, Orsay (FR); Enrico Baruffini, Parme (IT); Tiziana Lodi, Parme (IT); Agnes Rotig, Paris (FR); Vincent Procaccio, Avrille (FR)

(73) Assignees: UNIVERSITE PARIS-SUD, Orsay (FR); CENTRE NATIONAL DE LA RECHERCHE SCIENTIFIQUE, Paris (FR); UNIVERSITE D'ANGERS, Angers (FR); CENTRE HOSPITALIER UNIVERSITAIRE D'ANGERS, Angers (FR)

(*) Notice: Subject to any disclaimer, the term of this patent is extended or adjusted under 35 U.S.C. 154(b) by 161 days.

(21) Appl. No.: 15/532,011

(22) PCT Filed: Dec. 1, 2015

(86) PCT No.: PCT/FR2015/053286
§ 371 (c)(1),
(2) Date: May 31, 2017

(87) PCT Pub. No.: WO2016/087771
PCT Pub. Date: Jun. 9, 2016

(65) Prior Publication Data
US 2017/0266136 A1 Sep. 21, 2017

(30) Foreign Application Priority Data
Dec. 2, 2014 (FR) .................................. 14 61817

(51) Int. Cl.
A61K 31/138 (2006.01)
A61K 31/137 (2006.01)
A61K 31/14 (2006.01)
A61K 31/18 (2006.01)

(52) U.S. Cl.
CPC .......... A61K 31/138 (2013.01); A61K 31/137 (2013.01); A61K 31/14 (2013.01); A61K 31/18 (2013.01)

(58) Field of Classification Search
CPC .................................................... A61K 31/138
See application file for complete search history.

(56) References Cited

U.S. PATENT DOCUMENTS 4,289,787 A 9/1981 Molloy et al.

FOREIGN PATENT DOCUMENTS

| EP | 0 164 865 A1 | 12/1985 |
| EP | 0 245 997 A2 | 11/1987 |
| EP | 2 243 476 A1 | 10/2010 |
| WO | 99/07832 A1 | 2/1999 |
| WO | 2012/112933 A1 | 8/2012 |
| WO | 2013/148740 A1 | 10/2013 |

OTHER PUBLICATIONS

Caramia F et al.: "Mitochondrial lesions of developing sympathetic neurons induced by bretylium tosylate", Brain Research, Elsevier, Amsterdam, NL, vol. 40, No. 2, May 26, 1972 (May 26, 1972), pp. 237-246, XP024264641, ISSN: 0006-8993, [retrieved on May 26, 1972], DOI: 10.1016/0006-8993(72)90131-X.
Laras Pitayu: "Les maladies mitochondriales liees a l'instabilite d'ADN mitochondrial : de la therapie au mecanisme", Sep. 28, 2015 (Sep. 28, 2015), XP002753828, Retrieved from the Internet <URL:http://www.theses.fr/2015PA112233> [retrieved on Feb. 3, 2016].
International Search Report, dated Feb. 15, 2016, from corresponding PCT application.
FR Search Report, dated Jul. 31, 2015, from corresponding FR application.

Primary Examiner — Jeffrey S Lundgren
Assistant Examiner — Tori Strong
(74) Attorney, Agent, or Firm — Young & Thompson

(57) ABSTRACT

Disclosed is a compound of formula (Ia) for the use thereof in the treatment or prevention of diseases relating to the instability of mitochondrial DNA.

12 Claims, 15 Drawing Sheets

−: DMSO  +: CLOF 32 μM

COMPOUNDS FOR THE TREATMENT OF MITOCHONDRIAL DISEASES

The invention relates to compounds for use in the treatment and prevention of mitochondrial diseases.

Mitochondrial diseases comprise a very broad and heterogeneous group of rare diseases, which in particular includes disorders relating to the instability of mitochondrial DNA (mtDNA). Among them, progressive external ophthalmoplegia (PEO), neonatal liver failure and Alpers disease (Alpers-Huttenlocher syndrome, AHS) are caused by mutations in the gene encoding the polymerase gamma of mitochondrial DNA: the POLG gene (Spinazzola A, Zeviani M. Disorders of nuclear-mitochondrial intergenomic communication. *Biosci Rep* 2007; 27(1-3):39-51).

Mutations in the POLG gene can lead to accumulation of base substitutions, deletions in mtDNA and also mtDNA depletions, resulting in impaired energy production via oxidative phosphorylation.

So far, over 200 pathogenic mutations in the POLG gene have been reported. These mutations are associated with a very broad spectrum of mitochondrial diseases including, among others, PEO, myopathy, parkinsonism, premature menopause, psychological disorders, ataxia, encephalopathy and Alpers disease (Hudson G, Chinnery P F. Mitochondrial DNA polymerase-gamma and human disease. Hum Mol Genet. 2006; 15:R244-52). The dominant POLG mutations give rise to a progressive external ophthalmoplegia associated with multiple deletions of mtDNA, whereas the recessive mutations cause depletion of mtDNA (2-10% of the normal amount of mtDNA) and a neonatal liver failure or Alpers disease.

There is currently no curative treatment of diseases relating to the instability of mtDNA. The treatments are currently limited to symptom management and supportive care. A wide variety of vitamins and cofactors have been used in individuals suffering from mitochondrial disorders, although a recent systematic review has highlighted the lack of evidence supporting their use (Chinnery P, Majamaa K, Turnbull D, Thorburn D. Treatment for mitochondrial disorders. Cochrane Database Syst Rev. 2006 Jan. 25; (1): CD004426. Review. Update in: Cochrane Database Syst Rev. 2012; 4:CD004426). Levocarnitine, creatine monohydrate, the coenzyme $Q_{10}$, the B vitamins, and antioxidants, such as alpha-lipoic acid, vitamin E and vitamin C, have been used as mitochondrial supplements.

Thus, therapies based on vitamins and cofactors may be proposed in order to strengthen the mitochondrial functions. However, there have been no formal studies on the use of these vitamins and cofactors for Alpers disease or other diseases relating to the POLG gene (Parkih S, Saneto R, Falk M J, Anslem I, Cohen B H, Has R. A modem approach to the treatment of mitochondrial diseases. Current Treatment Options in Neurology. 2009; 11:414-430). It has also been reported that the use of levo-arginine helps reduce the frequency and severity of stroke associated with MELAS syndrome and could be considered in patients suffering from POLG-related diseases, especially if a deficiency in the plasma or a concentration of arginine in the cerebrospinal fluid is confirmed.

The use of treatments for refractory epilepsy, such as corticotropin or prednisone, ketogenic diet and intravenous immunoglobulins G, has not been shown to be effective in the treatment of AHS.

Liver transplantation among adults suffering from AHS and having an acceptable quality of life can be beneficial. However, liver transplantation is not recommended for children, since it will have no effect on the rapid progression of neurological damage (Kelly D A. Liver transplantation: to do or not to do? Pediatr Transplant. 2000; 4:170-2).

Clofilium tosylate is a class III antiarrhythmic agent of which the mechanism of action is based on blocking potassium channels, thus increasing the duration of cardiac action potentials (U.S. Pat. No. 4,289,787).

Ibutilide is a class III antiarrhythmic agent marketed under the name Corvert (as ibutilide fumarate) by Pfizer. This drug is used for the rapid reduction of atrial fibrillation or flutter to sinus rhythm. It works by delaying repolarisation by activation of a slow, essentially sodium-based, inward current (EP 0 164 865).

Dofetilide is a class III antiarrhythmic agent marketed by Pfizer under the name Tikosyn. It is prescribed for the treatment of atrial fibrillation and flutter. It works by blocking the potassium channels (EP 0 245 997).

One of the aims of the invention is to provide compounds effective in the treatment of mitochondrial diseases.

Another aspect of the invention is to provide compounds effective in the treatment of pathologies resulting from mutations in the POLG gene.

Another aspect of the invention is to provide compounds effective in the treatment of MELAS syndrome.

One advantage of the invention is to provide compounds effective in adults and in children.

Another advantage of the invention is to provide compounds which are suitable for the curative treatment of mitochondrial diseases and which are not limited to the management of symptoms of mitochondrial diseases.

The present invention relates to a compound having the formula I

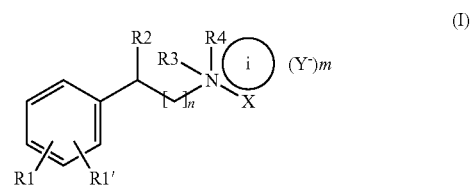

in which $R_1$ and $R_{1'}$ independently of one another represent a hydrogen atom, a halogen atom, in particular Cl or Br, a C1-C4 alkoxy group, a C1-C3 alkyl group, or $NHSO_2R_6$, on the condition that at least one of the two elements $R_1$ or $R_{1'}$ is different from H;

$R_2$ represents OH or H;

$R_3$ and $R_4$ independently of one another represent an alkyl group having 1 to 10 carbon atoms or

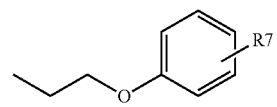

where $R_7$ represents a hydrogen atom, a halogen atom, a C1-C4 alkoxy group, a C1-C3 alkyl group, or $NHSO_2R_8$;

$R_6$ and $R_8$ independently of one another represent a C1-C4 alkyl group;

—X=—$R_5$ or the non-bonded electron pair of nitrogen, on the condition that i=+ when —X=—$R_5$;

$R_5$ represents a hydrogen atom or a C1-C4 alkyl group;
m=0 or 1, on the condition that m=1 when —X=—$R_5$ and m=0 when —X=the non-bonded electron pair of nitrogen;
n=0, 1, 2 or 3;
$Y^-$ is a therapeutically acceptable anion;
for use in the treatment or prevention of diseases relating to the instability of mitochondrial DNA.
Ø represents the empty set.

The invention relates in particular to a compound of formula I

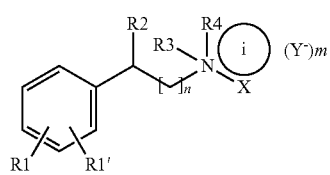

(I)

in which
$R_1$ and $R_{1'}$ independently of one another represent a hydrogen atom, a halogen atom, in particular Cl or Br, a C1-C4 alkoxy group, a C1-C3 alkyl group, or $NHSO_2R_6$, on the condition that at least one of the two elements $R_1$ or $R_{1'}$ is different from H;
$R_2$ represents OH or H;
$R_3$ and $R_4$ independently of one another represent an alkyl group having 1 to 10 carbon atoms or

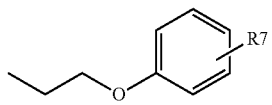

where $R_7$ represents a hydrogen atom, a halogen atom, a C1-C4 alkoxy group, a C1-C3 alkyl group, or $NHSO_2R_8$;
$R_6$ and $R_8$ independently of one another represent a C1-C4 alkyl group;
—X=—$R_5$ or the non-bonded electron pair of nitrogen, on the condition that i=+ when —X=—$R_5$;
$R_5$ represents a C1-C4 alkyl group;
m=0 or 1, on the condition that m=1 when —X=—$R_5$ and m=0 when —X=the non-bonded electron pair of nitrogen;
n=0, 1, 2 or 3;
$Y^-$ is a therapeutically acceptable anion; for use in the treatment or prevention of diseases relating to the instability of mitochondrial DNA.

In an especial embodiment of the invention, the compound of formula I as defined above, for use in the treatment or prevention of diseases relating to the instability of mitochondrial DNA, has an element $Y^-$ selected from the tosylate ion, the carbonate ion, the phosphate ion and the chloride ion.

The invention advantageously relates to a compound of formula I as defined above

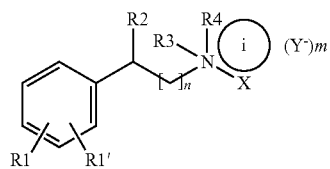

(I)

in which formula:
$R_1$ and $R_{1'}$ independently of one another represent a hydrogen atom, Cl, Br, or $NHSO_2R_6$, on the condition that at least one of the two elements $R_1$ or $R_{1'}$ is different from H;
$R_2$ represents OH or H;
$R_3$ and $R_4$ independently of one another represent an alkyl group having 1 to 10 carbon atoms or

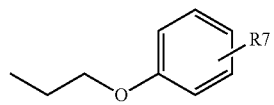

where $R_7$ represents a halogen atom or $NHSO_2R_8$, on the condition that $R_3$ and $R_4$ cannot simultaneously be

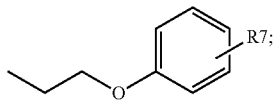

$R_6$ and $R_8$ independently of one another represent a C1-C4 alkyl group;
—X=—$R_5$ or the non-bonded electron pair of nitrogen, on the condition that i=+ when —X=—$R_5$;
$R_5$ represents a C1-C4 alkyl group;
m=0 or 1, on the condition that m=1 when —X=—$R_5$ and m=0 when —X=the non-bonded electron pair of nitrogen;
n=0, 1, 2 or 3;
$Y^-$ is selected from the tosylate ion, the carbonate ion, the phosphate ion and the chloride ion; for use in the treatment or prevention of diseases relating to the instability of mitochondrial DNA.

The present invention relates to a compound having the formula Ia:

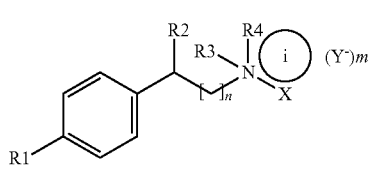

(Ia)

in which
$R_1$ represents a halogen atom, in particular Cl or Br, a C1-C4 alkoxy group, a C1-C3 alkyl group, or $NHSO_2R_6$;
$R_2$ represents OH or H;
$R_3$ and $R_4$ independently of one another represent an alkyl group having 1 to 10 carbon atoms or

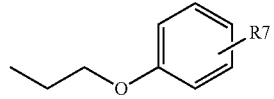

where $R_7$ represents a hydrogen atom, a halogen atom, a C1-C4 alkoxy group, a C1-C3 alkyl group, or $NHSO_2R_8$;
$R_6$ and $R_8$ independently of one another represent a C1-C4 alkyl group;
—X=—$R_5$ or the non-bonded electron pair of nitrogen, on the condition that i=+ when —X=—$R_5$;

$R_5$ represents a hydrogen atom or a C1-C4 alkyl group;
m=0 or 1, on the condition that m=1 when —X=—$R_5$ and m=0 when —X=the non-bonded electron pair of nitrogen;
n=0, 1, 2 or 3;
$Y^-$ is a therapeutically acceptable anion;
for use in the treatment or prevention of diseases relating to the instability of mitochondrial DNA.

The inventors have unexpectedly found that the application of compounds of the invention to organisms suffering from a mitochondrial disease allows an improvement in their condition. This invention is based in particular on the results obtained by applying the compounds defined above to organisms mimicking mitochondrial disease or cell cultures of skin fibroblasts from a patient suffering from mitochondrial disease, or cell cultures of neuronal cybrids derived from a patient suffering from a mitochondrial disease.

The term "Cx-Cy alkoxy group" means an alkyl group having from x to y carbon atoms, bonded to an oxygen atom.

The term "Cx-Cy alkyl group" means a saturated hydrocarbon chain—linear or branched—containing from x to y carbon atoms.

The term "X=—$R_5$" means that the amine to which the $R_5$ group is linked is a quaternary amine, and that in this case i=+ and m=1, the compound then being in salt form.

The term "X=the non-bonded electron pair of nitrogen" means that the corresponding amine is a tertiary amine and that in this case i=Ø, m=0 and $(Y^-)_m$=Ø.

The term "quaternary amine" means that the nitrogen atom is positively charged, that is to say it is in the form of a cation, and it is substituted with 4 substituents. Within the meaning of the present invention, one of the substituents can be a hydrogen atom.

The term "tertiary amine" means that the nitrogen atom is substituted with 3 substituents.

The term "therapeutically acceptable anion" means any non-toxic anion that does not induce a loss of therapeutic or prophylactic effect of the cation to which it is linked.

The term "instability of mitochondrial DNA" means the presence of any mutations, deletions and/or depletions of the mitochondrial DNA compared to the mitochondrial DNA of a healthy individual.

In the sense of the present invention, the term "diseases relating to the instability of mitochondrial DNA" means diseases relating to the quantitative aspect of the instability of mitochondrial DNA and diseases relating to the qualitative aspect of the instability of mitochondrial DNA.

The term "diseases relating to the quantitative aspect of the instability of mitochondrial DNA" means diseases relating to a depletion of the mitochondrial DNA. This depletion may be due in particular to one or more mutations present in the POLG gene, which is a nuclear gene encoding the POLG polymerase specific to mitochondrial DNA.

The term "depletion of the mitochondrial DNA" means a reduction in the number of copies of mitochondrial DNA molecules in the mitochondria of an organism compared to a healthy organism. The depletions are tissue-specific.

The term "diseases relating to the qualitative aspect of the instability of mitochondrial DNA" means diseases of which the cause lies in the presence of deletions and/or mutations in the mitochondrial DNA.

The expression "deletion of mitochondrial DNA" means a loss of genetic material in the mitochondrial DNA compared to a wild-type mitochondrial DNA. A deletion can involve one or more nucleotides, in particular several hundred nucleotides, of mitochondrial DNA.

The expression "mutation of mitochondrial DNA" means a change in mitochondrial DNA compared to a wild-type mitochondrial DNA. The mutations include mutations by substitution, mutations by insertion, and mutations by deletions that are small in size (1 to 10 nucleotides). The term "mutation by substitution" means the replacement of one or more nucleotides with a different nucleotide in the mitochondrial DNA molecule. The term "mutation by insertion" means the addition of one or more nucleotides in the mitochondrial DNA molecule.

Diseases relating to the instability of mitochondrial DNA include, but are not limited to, Alpers-Huttenlocher syndrome (AHS), childhood myocerebrohepatopathy spectrum (MCHS), myoclonic epilepsy myopathy sensory ataxia (MEMSA), spinocerebellar ataxia with epilepsy (SCAE), ataxia with neuropathy syndromes including MIRAS and SANDO, autosomal recessive progressive external ophthalmoplegia (arPEO), autosomal dominant progressive external ophthalmoplegia (adPEO), mitochondrial neurogastrointestinal encephalopathy (MNGIE), infantile myopathy and spinal muscular atrophy relating to TK2 mutations, liver failure with depletion of mtDNA, pathologies associated with mutations of the genes SUCLA2 and SUCLAG1, RRM2B, AIF1, MPV17, Leber hereditary optic neuropathy, MELAS syndrome, MERRF syndrome, and some forms of Leigh syndrome, chronic progressive external ophthalmoplegia, myopathy, cardiomyopathy, diabetes-deafness, encephalomyopathy, and deafness.

In an especial embodiment of the invention, the compound of formula Ia as defined above, for use in the treatment or prevention of diseases relating to the instability of mitochondrial DNA, contains an element $Y^-$ selected from the tosylate ion, the carbonate ion, the phosphate ion and the chloride ion.

In an especial embodiment, the invention relates to a compound as defined above, of the formula Ia:

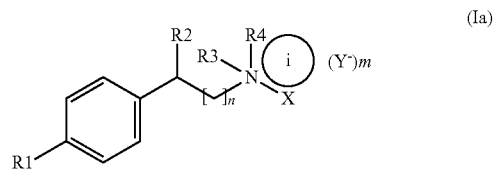

in which
$R_1$ represents Cl, Br, or $NHSO_2R_6$;
$R_2$ represents OH or H;
$R_3$ and $R_4$ independently of one another represent an alkyl group having 1 to 10 carbon atoms or

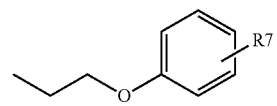

where $R_7$ represents a halogen atom or $NHSO_2R_8$, on the condition that $R_3$ and $R_4$ cannot simultaneously be

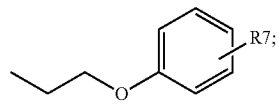

$R_6$ and $R_8$ independently of one another represent a C1-C4 alkyl group;

—X=—$R_5$ or the non-bonded electron pair of nitrogen, on the condition that i=+ when —X=—$R_5$;

$R_5$ represents a C1-C4 alkyl group;

m=0 or 1, on the condition that m=1 when —X=—$R_5$ and m=0 when —X=the non-bonded electron pair of nitrogen;

n=0, 1, 2 or 3;

$Y^-$ is selected from the tosylate ion, the carbonate ion, the phosphate ion and the chloride ion;

for use in the treatment or prevention of diseases relating to the instability of mitochondrial DNA.

In an especial embodiment, the invention relates to a compound as defined above, of formula Iaa:

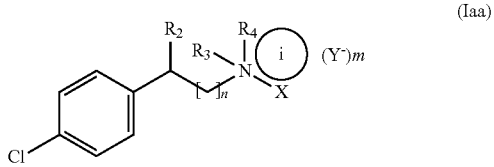

(Iaa)

in which $R_2$ represents OH or H;

$R_3$ and $R_4$ independently of one another represent an alkyl group having 1 to 10 carbon atoms or

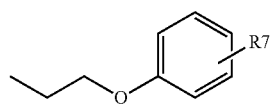

where $R_7$ represents a hydrogen atom, a halogen atom, a C1-C4 alkoxy group, a C1-C3 alkyl group, or $NHSO_2R_8$;

$R_8$ represents a C1-C4 alkyl group;

—X=—$R_5$ or the non-bonded electron pair of nitrogen, on the condition that i=+ when —X=—$R_5$;

$R_5$ represents a hydrogen atom or a C1-C4 alkyl group;

m=0 or 1, on the condition that m=1 when —X=—$R_5$ and m=0 when —X=the non-bonded electron pair of nitrogen;

n=0, 1, 2 or 3;

$Y^-$ is a therapeutically acceptable ion;

for use in the treatment or prevention of diseases relating to the instability of mitochondrial DNA.

In another especial embodiment, the invention relates to a compound as defined above, of formula Iab:

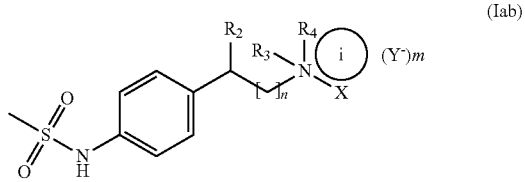

(Iab)

in which $R_2$ represents OH or H;

$R_3$ and $R_4$ independently of one another represent an alkyl group having 1 to 10 carbon atoms or

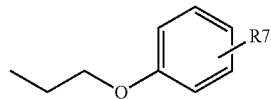

where $R_7$ represents a hydrogen atom, a halogen atom, a C1-C4 alkoxy group, a C1-C3 alkyl group, or $NHSO_2R_8$;

$R_8$ represents a C1-C4 alkyl group;

—X=—$R_5$ or the non-bonded electron pair of nitrogen, on the condition that i=+ when —X=—$R_5$;

$R_5$ represents a hydrogen atom or a C1-C4 alkyl group;

m=0 or 1, on the condition that m=1 when —X=—$R_5$ and m=0 when —X=the non-bonded electron pair of nitrogen;

n=0, 1, 2 or 3;

$Y^-$ is a therapeutically acceptable ion;

for use in the treatment or prevention of diseases relating to the instability of mitochondrial DNA.

In another especial embodiment, the invention relates to a compound of formula Ib

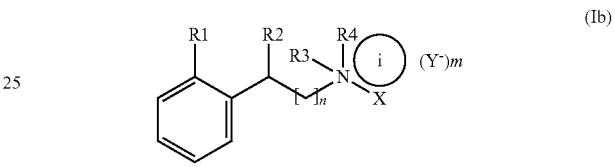

(Ib)

in which $R_1$ represents a halogen atom, in particular Cl or Br, a C1-C4 alkoxy group, a C1-C3 alkyl group, or $NHSO_2R_6$;

$R_2$ represents OH or H;

$R_3$ and $R_4$ independently of one another represent an alkyl group having 1 to 10 carbon atoms or

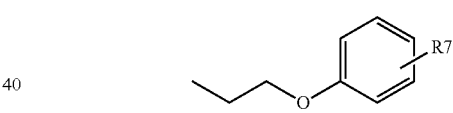

where $R_7$ represents a hydrogen atom, a halogen atom, a C1-C4 alkoxy group, a C1-C3 alkyl group, or $NHSO_2R_8$;

$R_6$ and $R_8$ independently of one another represent a C1-C4 alkyl group;

—X=—$R_5$ or the non-bonded electron pair of nitrogen, on the condition that i=+ when —X=—$R_5$;

$R_5$ represents a hydrogen atom or a C1-C4 alkyl group;

m=0 or 1, on the condition that m=1 when —X=—$R_5$ and m=0 when —X=the non-bonded electron pair of nitrogen;

n=0, 1, 2 or 3;

$Y^-$ is a therapeutically acceptable anion;

for use in the treatment or prevention of diseases relating to the instability of mitochondrial DNA.

In an especial embodiment, the invention relates to a compound of formula Ic

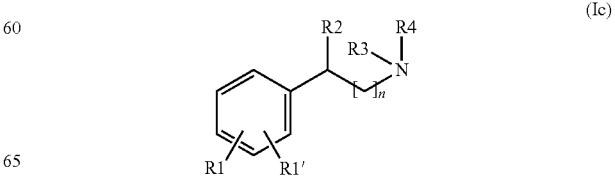

(Ic)

in which
R₁ and R₁' independently of one another represent a hydrogen atom, a halogen atom, in particular Cl or Br, a C1-C4 alkoxy group, a C1-C3 alkyl group, or NHSO₂R₆, on the condition that at least one of the two elements R₁ or R₁' is different from H;
R₂ represents OH or H;
R₃ and R₄ independently of one another represent an alkyl group having 1 to 10 carbon atoms or

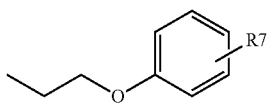

where R₇ represents a hydrogen atom, a halogen atom, a C1-C4 alkoxy group, a C1-C3 alkyl group, or NHSO₂R₈;
R₆ and R₈ independently of one another represent a C1-C4 alkyl group; n=0, 1, 2 or 3;
for use in the treatment or prevention of diseases relating to the instability of mitochondrial DNA.

The amino group bearing the groups R₃ and R₄ of the compound of formula Ic is a tertiary amine.

In another especial embodiment, the invention relates to a compound of formula Id

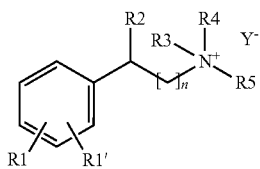

(Id)

in which
R₁ and R₁' independently of one another represent a hydrogen atom, a halogen atom, in particular Cl or Br, a C1-C4 alkoxy group, a C1-C3 alkyl group, or NHSO₂R₆, on the condition that at least one of the two elements R₁ or R₁' is different from H;
R₂ represents OH or H;
R₃ and R₄ independently of one another represent an alkyl group having 1 to 10 carbon atoms or

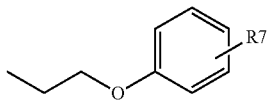

where R₇ represents a hydrogen atom, a halogen atom, a C1-C4 alkoxy group, a C1-C3 alkyl group, or NHSO₂R₈;
R₆ and R₈ independently of one another represent a C1-C4 alkyl group;
R₅ represents a hydrogen atom or a C₁-C₄ alkyl group;
n=0, 1, 2 or 3;
Y⁻ is a therapeutically acceptable anion;
for use in the treatment or prevention of diseases relating to the instability of mitochondrial DNA.

The amino group bearing the groups R₃, R₄ and R₅ of the compound of formula Id is a quaternary amine.

In an advantageous embodiment, the compound of the invention as defined above has for formula (a):

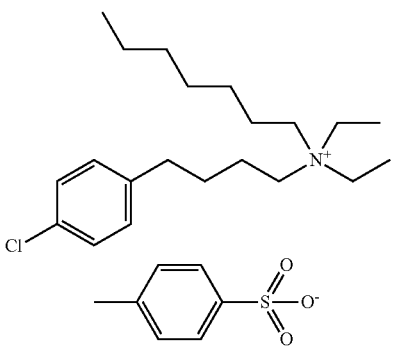

(a)

The compound of formula (a) is clofilium tosylate, the compound of formula:

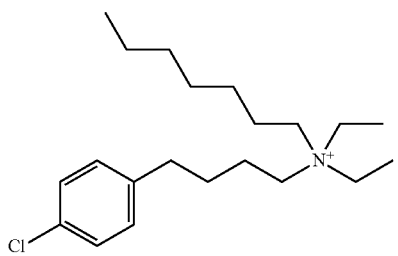 [SMILES: CCCCCCC[N+](CC)(CC)CCCCc1ccc(Cl)cc1]

being clofilium,
and the compound of formula:

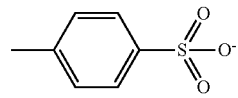

being the tosylate ion.

In another advantageous embodiment, the compound of the invention as defined above has for formula (b):

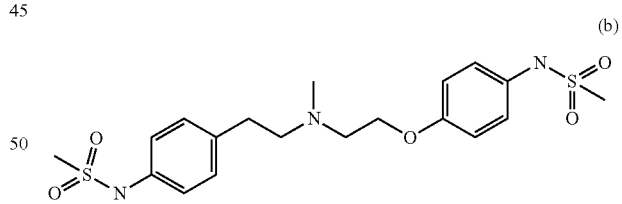

(b)

The compound of formula (b) is dofetilide.

In another advantageous embodiment, the compound of the invention as defined above has for formula (c):

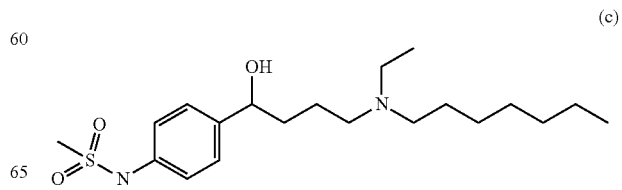

(c)

The compound of formula (c) is ibutilide.

In an especial embodiment, the invention relates to a compound of formula (a), (b) or (c), for administration at a dose of from 1 µg kg to 50 mg/kg, for use in the treatment or prevention of diseases relating to the instability of mitochondrial DNA.

Especially, the invention relates to a compound of formula (a), (b) or (c), for administration at a dose of from 1 to 50 µg/kg, from 50 to 500 µg/kg, from 500 µg to 5 mg/kg, or from 5 to 50 mg/kg, even more especially at a dose of from 1 to 12 µg/kg, from 12 to 20 µg/kg, from 20 to 50 µg/kg, from 20 to 300 µg/kg, from 50 to 300 µg/kg, from 300 to 500 µg/kg, from 500 µg/kg to 1 mg/kg, from 1 to 5 mg/kg, from 5 to 30 mg/kg, or from 30 to 50 mg/kg, for use in the treatment or prevention of diseases relating to the instability of mitochondrial DNA.

In another especial embodiment, the invention relates to a compound of formula (a), (b) or (c), in the form of a unit dose of from 30 µg to 6000 mg, for use in the treatment or prevention of diseases relating to the instability of mitochondrial DNA.

In the sense of the present invention, the term "unit dose" means the dose corresponding to the total dose of the compound taken at once, regardless of the method of administration of the compound.

Especially, the invention relates to a compound of formula (a), (b) or (c), in the form of a unit dose of from 30 to 500 µg, from 500 µg to 2.5 mg, from 2.5 to 60 mg, from 60 to 150 mg, or from 150 to 6000 mg, even more especially in the form of a unit dose of from 30 to 150 µg, from 150 to 300 µg, from 300 to 500 µg, from 500 µg to 1 mg, from 1 to 2.5 mg, from 2.5 to 30 mg, from 30 mg to 60 mg, from 150 to 2500 mg, from 2500 to 4500 mg or from 4500 to 6000 mg, for use in the treatment or prevention of diseases relating to the instability of mitochondrial DNA.

In an especial embodiment, the invention relates to a compound of formula (a), (b) or (c), for oral administration at a dose of from 1 µg/kg to 50 mg/kg, for use in the treatment or prevention of diseases relating to the instability of mitochondrial DNA.

Especially, the invention relates to a compound of formula (a), (b) or (c), for oral administration in a dose of from 1 to 50 µg/kg, from 50 to 500 µg/kg, from 500 µg/kg to 5 mg/kg, or from 5 to 50 mg/kg, even more especially at a dose of from 1 to 20 µg/kg, from 20 to 50 µg/kg, from 50 to 300 µg/kg, from 300 to 500 µg/kg, from 500 µg/kg to 1 mg/kg, from 1 to 5 mg/kg, from 5 to 30 mg/kg, or from 30 to 50 mg/kg, for use in the treatment or prevention of diseases relating to the instability of mitochondrial DNA.

In another especial embodiment, the invention relates to a compound of formula (a), (b) or (c), in the form of a unit dose of from 30 µg to 6000 mg, for oral administration, for use in the treatment or prevention of diseases relating to the instability of mitochondrial DNA.

Especially, the invention relates to a compound of formula (a), (b) or (c), in the form of a unit dose of from 30 to 500 µg, from 500 µg to 60 mg, or from 60 mg to 6000 mg, even more especially in the form of a unit dose of from 30 to 125 µg, from 125 to 300 µg, from 300 to 500 µg, from 500 µg to 1.5 mg, from 1.5 to 25 mg, from 25 to 60 mg, from 60 to 500 mg, from 500 to 2000 mg, or from 2000 to 6000 mg, for oral administration, for use in the treatment or prevention of diseases relating to the instability of mitochondrial DNA.

In another especial embodiment, the invention relates to a compound of formula (a), (b) or (c), for intravenous administration at a dose of from 1 µg/kg to 50 mg/kg, for use in the treatment or prevention of diseases relating to the instability of mitochondrial DNA.

Especially, the invention relates to a compound of formula (a), (b) or (c), for intravenous administration at a dose of from 1 to 20 µg/kg, from 20 to 500 µg/kg, from 500 µg/kg to 5 mg/kg, or from 5 to 50 mg/kg, even more especially at a dose of from 1 to 12 µg/kg, from 12 to 20 µg/kg, from 20 to 50 µg/kg, from 20 to 150 µg/kg, from 50 to 300 µg/kg, from 300 to 500 µg/kg, from 500 µg/kg to 1 mg/kg, from 1 to 5 mg/kg, from 5 to 30 mg/kg, or from 30 to 50 mg kg, for use in the treatment or prevention of diseases relating to the instability of mitochondrial DNA.

In another especial embodiment, the invention relates to a compound of formula (a), (b) or (c), in the form of a unit dose of from 30 µg to 6000 mg, for intravenous administration, for use in the treatment or prevention of diseases relating to the instability of mitochondrial DNA.

Especially, the invention relates to a compound of formula (a), (b) or (c), in the form of a unit dose of from 30 to 500 µg, from 500 µg to 30 mg, from 30 to 150 mg, or from 150 to 6000 mg, even more especially in the form of a unit dose of from 30 to 150 µg, from 150 to 500 µg, from 500 µg to 1.5 mg, from 1.5 to 30 mg, from 30 to 60 mg, from 60 to 150 mg, from 150 to 1000 mg, from 1000 to 2500 mg, or from 2500 to 6000 mg, for intravenous administration, for use in the treatment or prevention of diseases relating to the instability of mitochondrial DNA.

In another especial embodiment, the invention relates to a compound of formula (a), (b) or (c) for administration at a dose of from 0.1 µg/kg to 5 mg/kg, for use in the treatment or prevention of diseases relating to the instability of mitochondrial DNA.

Especially, the invention relates to a compound of formula (a), (b) or (c), for administration at a dose of from 0.1 to 5 µg kg, from 5 to 50 µg/kg, from 50 µg/kg to 0.5 mg/kg, or from 0.5 to 5 mg/kg, even more especially at a dose of from 0.1 to 1.2 µg/kg, from 1.2 to 2 µg/kg, from 2 to 5 µg/kg, from 2 to 30 µg/kg, from 5 to 30 µg/kg, from 30 to 50 µg/kg, from 50 µg/kg to 100 µg/kg, from 100 to 500 µg/kg, from 500 µg/kg to 3 mg/kg, or from 3 to 5 mg/kg, for use in the treatment or prevention of diseases relating to the instability of mitochondrial DNA.

In another especial embodiment, the invention relates to a compound of formula (a), (b) or (c), in the form of a unit dose of from 3 µg to 600 mg, for use in the treatment or prevention of diseases relating to the instability of mitochondrial DNA.

Especially, the invention relates to a compound of formula (a), (b) or (c), in the form of a unit dose of from 3 to 50 µg, from 50 µg to 250 µg, from 250 µg to 6 mg, from 6 to 15 mg, or from 15 to 600 mg, even more especially in the form of a unit dose of from 3 to 15 µg, from 15 to 30 µg, from 30 to 50 µg, from 50 µg to 0.1 mg, from 0.1 to 0.25 mg, from 0.25 to 3 mg, from 3 mg to 6 mg, from 15 to 250 mg, from 250 to 450 mg, or from 450 mg to 600 mg, for use in the treatment or prevention of diseases relating to the instability of mitochondrial DNA.

In an especial embodiment, the invention relates to a compound of formula (a), (b) or (c), for oral administration at a dose of from 0.1 µg/kg to 5 mg/kg, for use in the treatment or prevention of diseases relating to the instability of mitochondrial DNA.

Especially, the invention relates to a compound of formula (a), (b) or (c), for oral administration at a dose of from 0.1 to 5 µg/kg, from 5 to 50 µg/kg, from 50 µg/kg to 0.5 mg/kg, or from 0.5 to 5 mg/kg, even more especially at a dose of from 0.1 to 2 µg/kg, from 2 to 5 µg/kg, from 5 to 30 µg/kg, from 30 to 50 µg/kg, from 50 µg/kg to 100 µg/kg, from 100 µg/kg to 500 µg/kg, from 500 µg/kg to 3 mg/kg, or from 3 to 5 mg/kg, for use in the treatment or prevention of diseases relating to the instability of mitochondrial DNA.

In another especial embodiment, the invention relates to a compound of formula (a), (b) or (c), in the form of a unit dose of from 3 µg to 600 mg, for oral administration, for use in the treatment or prevention of diseases relating to the instability of mitochondrial DNA.

Especially, the invention relates to a compound of formula (a), (b) or (c), in the form of a unit dose of from 3 to 50 µg, from 50 µg to 6 mg, or from 6 mg to 600 mg, even more especially in the form of a unit dose of from 3 to 12.5 µg, from 12.5 to 30 µg, from 30 to 50 µg, from 50 µg to 150 µg, from 150 µg to 2.5 mg, from 2.5 to 6 mg, from 6 to 50 mg, from 50 to 200 mg, or from 200 to 600 mg, for oral administration, for use in the treatment or prevention of diseases relating to the instability of mitochondrial DNA.

In another especial embodiment, the invention relates to a compound of formula (a), (b) or (c), for intravenous administration at a dose of from 0.1 µg/kg to 5 mg/kg, for use in the treatment or prevention of diseases relating to the instability of mitochondrial DNA.

Especially, the invention relates to a compound of formula (a), (b) or (c), for intravenous administration at a dose of from 0.1 to 2 µg/kg, from 2 to 50 µg/kg, from 50 µg/kg to 0.5 mg/kg, or from 0.5 to 5 mg/kg, even more especially at a dose of from 0.1 to 1.2 µg/kg, from 1.2 to 2 µg/kg, from 2 to 5 µg/kg, from 2 to 15 µg/kg, from 5 to 30 µg/kg, from 30 to 50 µg/kg, from 50 µg/kg to 100 µg/kg, from 100 to 500 µg/kg, from 500 µg/kg to 3 mg/kg, or from 3 to 5 mg/kg, for use in the treatment or prevention of diseases relating to the instability of mitochondrial DNA.

In another especial embodiment, the invention relates to a compound of formula (a), (b) or (c), in the form of a unit dose of from 3 µg to 600 mg, for intravenous administration, for use in the treatment or prevention of diseases relating to the instability of mitochondrial DNA.

Especially, the invention relates to a compound of formula (a), (b) or (c), in the form of a unit dose of from 3 to 50 µg, from 50 µg to 3 mg, from 3 to 15 mg, or from 15 to 600 mg, even more especially in the form of a unit dose of from 3 to 15 µg, from 15 to 50 µg, from 50 µg to 0.15 mg, from 0.15 to 3 mg, from 3 to 6 mg, from 6 to 15 mg, from 15 to 100 mg, 100 to 250 mg, or from 250 to 600 mg, for intravenous administration, for use in the treatment or prevention of diseases relating to the instability of mitochondrial DNA.

In an even more especial embodiment, the invention relates to a compound of formula (a):

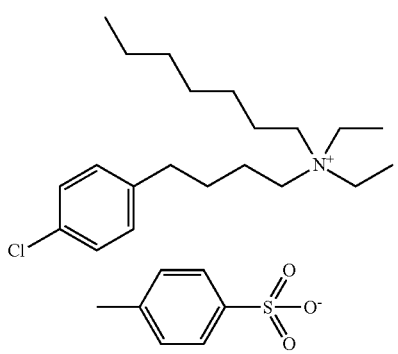

(a)

for oral administration at a dose of from 50 to 500 µg/kg, for use in the treatment or prevention of diseases relating to the instability of mitochondrial DNA.

Especially, the invention relates to a compound of formula (a), for oral administration at a dose of from 50 to 300 µg/kg, or from 300 to 500 µg/kg, even more especially at a dose of from 50 to 100 µg/kg, from 100 to 200 µg/kg, from 200 to 300 µg/kg, from 300 to 400 µg/kg, or from 400 to 500 µg/kg, for use in the treatment or prevention of diseases relating to the instability of mitochondrial DNA.

In another especial embodiment, the invention relates to a compound of formula (a):

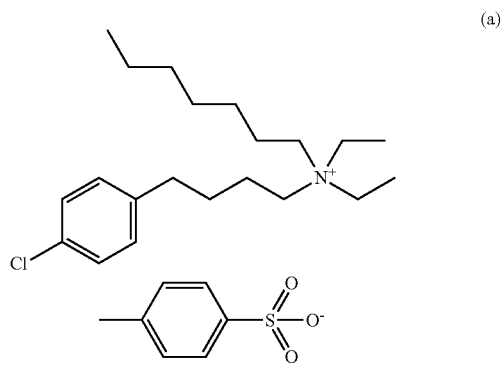

(a)

in the form of a unit dose of from 1.5 mg to 60 mg, for oral administration, for use in the treatment or prevention of diseases relating to the instability of mitochondrial DNA.

Especially, the invention relates to a compound of formula (a), in the form of a unit dose of from 1.5 to 25 mg, or from 25 to 60 mg, even more especially from 1.5 to 8 mg, from 8 to 15 mg, from 15 to 25 mg, from 25 to 35 mg, from 35 to 60 mg, from 35 to 45 mg, or from 45 to 60 mg, for oral administration, for use in the treatment or prevention of diseases relating to the instability of mitochondrial DNA.

In another especial embodiment, the invention relates to a compound of formula (a):

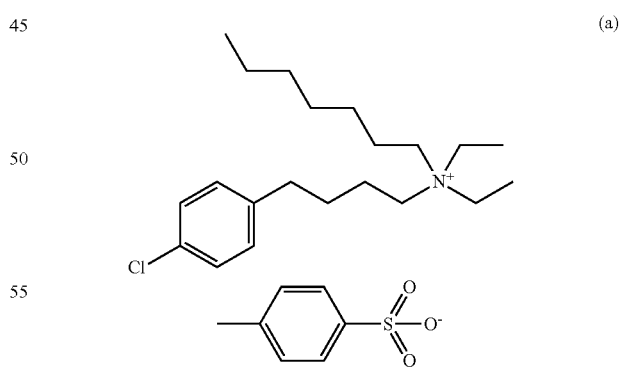

(a)

for intravenous administration at a dose of from 20 to 250 µg/kg, for use in the treatment or prevention of diseases relating to the instability of mitochondrial DNA.

Especially, the invention relates to a compound of formula (a), for intravenous administration at a dose of from 20 to 150 mg/kg, or from 150 to 250 mg/kg, even more especially at a dose of from 20 to 50 mg/kg, from 50 to 100 µg/kg, from 100 to 150 µg/kg, from 150 to 200 mg/kg, or from 200 to 250 mg/kg, for use in the treatment or prevention of diseases relating to the instability of mitochondrial DNA.

In another especial embodiment, the invention relates to a compound of formula (a):

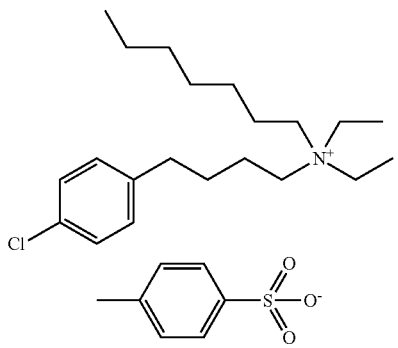

(a)

in the form of a unit dose of from 0.5 mg to 30 mg, for intravenous administration, for use in the treatment or prevention of diseases relating to the instability of mitochondrial DNA.

Especially, the invention relates to a compound of formula (a), in the form of a unit dose of from 0.5 mg to 12 mg, or from 12 to 30 mg, even more especially in the form of a unit dose of from 0.5 to 4 mg, from 4 to 8 mg, from 8 to 12 mg, from 12 to 16 mg, from 16 to 30 mg, from 16 to 20 mg, or from 20 to 30 mg, for intravenous administration, for use in the treatment or prevention of diseases relating to the instability of mitochondrial DNA.

In another especial embodiment, the invention relates to a compound of formula (a):

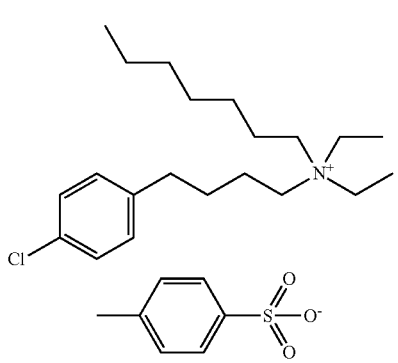

(a)

for oral administration at a dose of from 5 to 50 µg/kg, for use in the treatment or prevention of diseases relating to the instability of mitochondrial DNA.

Especially, the invention relates to a compound of formula (a), for oral administration at a dose of from 5 to 30 µg/kg, or from 30 to 50 µg/kg, even more especially at a dose of from 5 to 10 µg/kg, from 10 to 20 µg/kg, from 20 to 30 µg/kg, from 30 to 40 µg/kg, or from 40 to 50 µg/kg, for use in the treatment or prevention of diseases relating to the instability of mitochondrial DNA.

In another especial embodiment, the invention relates to a compound of formula (a), in the form of a unit dose of from 150 µg to 6 mg, for oral administration, for use in the treatment or prevention of diseases relating to the instability of mitochondrial DNA.

Especially, the invention relates to a compound of formula (a), in the form of a unit dose of from 150 µg to 2.5 mg or from 2.5 to 6 mg, even more especially from 150 µg to 800 µg, from 800 µg to 1.5 mg, from 1.5 to 2.5 mg, from 2.5 to 3.5 mg, from 3.5 to 6 mg, from 3.5 to 4.5 mg, or from 4.5 to 6 mg, for oral administration, for use in the treatment or prevention of diseases relating to the instability of mitochondrial DNA.

In another especial embodiment, the invention relates to a compound of formula (a), for intravenous administration at a dose of from 2 to 25 µg/kg, for use in the treatment or prevention of diseases relating to the instability of mitochondrial DNA.

Especially, the invention relates to a compound of formula (a), for intravenous administration at a dose of from 2 to 15 µg/kg or from 15 to 25 µg/kg, even more especially at a dose of from 2 to 5 µg/kg, from 5 to 10 µg/kg, from 10 to 15 µg/kg, from 15 to 20 µg/kg, or from 20 to 25 µg/kg, for use in the treatment or prevention of diseases relating to the instability of mitochondrial DNA.

In another especial embodiment, the invention relates to a compound of formula (a), in the form of a unit dose of from 50 µg to 3 mg, for intravenous administration, for use in the treatment or prevention of diseases relating to the instability of mitochondrial DNA.

Especially, the invention relates to a compound of formula (a), in the form of a unit dose of from 50 µg to 1.2 mg or from 1.2 to 3 mg, even more especially in the form of a unit dose of from 50 µg to 400 µg, from 400 to 800 µg, from 800 µg to 1.2 mg, from 1.2 to 1.6 mg, from 1.6 to 3 mg, from 1.6 mg to 2 mg, or from 2 to 3 mg, for intravenous administration, for use in the treatment or prevention of diseases relating to the instability of mitochondrial DNA.

In another especial embodiment, the invention relates to a compound of formula (b):

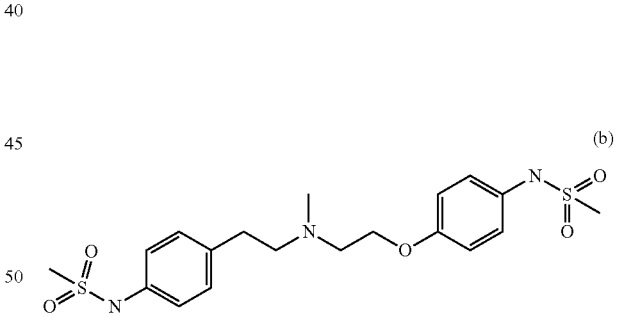

(b)

in the form of a unit dose of from 125 to 500 µg twice per day, for oral administration, for use in the treatment or prevention of diseases relating to the instability of mitochondrial DNA.

Especially, the invention relates to a compound of formula (b), in the form of a unit dose of from 125 to 300 µg or from 300 to 500 µg twice per day, even more especially in the form of a unit dose of from 125 to 200 µg, from 200 to 300 µg, from 300 to 400 µg, or from 400 to 500 µg twice per day, for oral administration, for use in the treatment or prevention of diseases relating to the instability of mitochondrial DNA.

In another especial embodiment, the invention relates to a compound of formula (b):

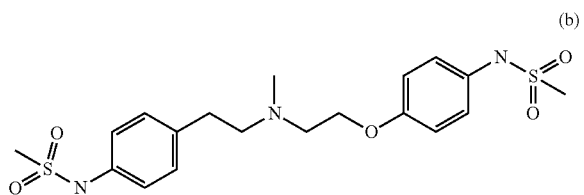 [SMILES: CN(CCOc1ccc(NS(C)(=O)=O)cc1)CCc1ccc(NS(C)(=O)=O)cc1]

(b)

in the form of a unit dose of from 12.5 to 50 µg, for oral administration, for use in the treatment or prevention of diseases relating to the instability of mitochondrial DNA.

Especially, the invention relates to a compound of formula (b), in the form of a unit dose of from 12.5 to 30 µg or from 30 to 50 µg, even more especially in the form of a unit dose of from 12.5 to 20 µg, from 20 to 30 µg, from 30 to 40 µg, or from 40 to 50 µg, for oral administration, for use in the treatment or prevention of diseases relating to the instability of mitochondrial DNA.

In another especial embodiment, the invention relates to a compound of formula (c):

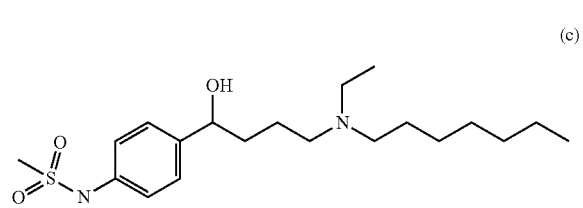 [SMILES: CCCCCCCN(CC)CCCC(O)c1ccc(NS(C)(=O)=O)cc1]

(c)

for intravenous administration at a dose of from 5 µg/kg to 20 µg/kg, for use in the treatment or prevention of diseases relating to the instability of mitochondrial DNA.

Especially, the invention relates to a compound of formula (c), for intravenous administration at a dose of from 5 to 12 µg/kg, or from 12 to 20 µg/kg, even more especially at a dose of from 5 to 8 µg/kg, from 8 to 12 µg/kg, from 12 to 16 µg/kg, or from 16 to 20 µg/kg, for use in the treatment or prevention of diseases relating to the instability of mitochondrial DNA.

In another especial embodiment, the invention relates to a compound of formula (c):

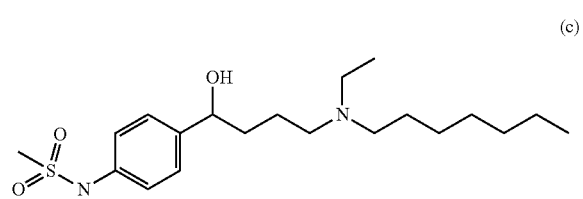 [SMILES: CCCCCCCN(CC)CCCC(O)c1ccc(NS(C)(=O)=O)cc1]

(c)

in the form of a unit dose of from 150 µg to 2500 µg, for intravenous administration, for use in the treatment or prevention of diseases relating to the instability of mitochondrial DNA.

Especially, the invention relates to a compound of formula (c), in the form of a unit dose of from 150 to 1000 µg or from 1000 to 2500 µg, even more especially in the form of a unit dose of from 150 to 650 µg, from 650 to 1000 µg, from 1000 to 1500 µg, from 1500 to 2500 µg, from 1500 to 2000 µg, or from 2000 to 2500 µg, for intravenous administration, for use in the treatment or prevention of diseases relating to the instability of mitochondrial DNA.

In another embodiment, the invention relates to a compound of formula (c):

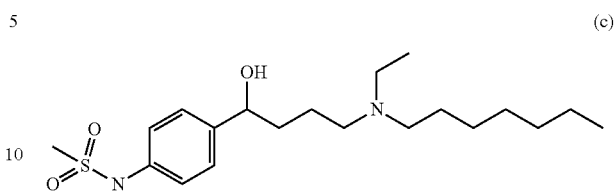

(c)

for intravenous administration at a dose of from 0.5 µg/kg to 2 µg/kg, for use in the treatment or prevention of diseases relating to the instability of mitochondrial DNA.

Especially, the invention relates to a compound of formula (c), for intravenous administration at a dose of from 0.5 to 1.2 µg/kg or from 1.2 to 2 µg/kg, even more especially at a dose of from 0.5 to 0.8 µg/kg, from 0.8 to 1.2 µg/kg, from 1.2 to 1.6 µg/kg, or from 1.6 to 2 µg/kg, for use in the treatment or prevention of diseases relating to the instability of mitochondrial DNA.

In another especial embodiment, the invention relates to a compound of formula (c), in the form of a unit dose of from 15 µg to 250 µg, for intravenous administration, for use in the treatment or prevention of diseases relating to the instability of mitochondrial DNA.

Especially, the invention relates to a compound of formula (c), in the form of a unit dose of from 15 to 100 µg or from 100 to 250 µg, even more especially in the form of a unit dose of from 15 to 65 µg, from 65 to 100 µg, from 100 to 150 µg, from 150 to 250 µg, from 150 to 200 µg, or from 200 to 250 µg, for intravenous administration, for use in the treatment or prevention of diseases relating to the instability of mitochondrial DNA.

Advantageously, the invention relates to a compound of formula (a), (b) or (c), in the form of an injectable solution, syrup, suspension, powder, capsule, tablet, pellet, granule, pill or suppository, for use in the treatment or prevention of diseases relating to the instability of mitochondrial DNA.

In an especial embodiment, the invention relates to a compound of formula (a), (b) or (c), for oral administration, in the form of a syrup, suspension, powder, capsule, tablet, pellet, granule or pill, for use in the treatment or prevention of diseases relating to the instability of mitochondrial DNA.

Advantageously, the invention relates to a compound as defined above, for use in the treatment or prevention of diseases relating to at least one mutation, or at least one deletion or at least one insertion, or a combination thereof, in the POLG gene.

In another embodiment, the invention relates to a compound as defined above, for use in the treatment or prevention of diseases relating to the instability of mitochondrial DNA unrelated to mutations of the POLG gene.

In an especial embodiment, the invention relates to a compound as defined above, for use in the treatment or prevention of diseases relating to a depletion or deletion of mitochondrial DNA.

In another especial embodiment, the invention relates to a compound as defined above, for use in the treatment or prevention of diseases relating to a point mutation in the mitochondrial DNA.

In an even more especial embodiment, the invention relates to a compound as defined above, for use in the treatment or prevention of diseases associated with quantitative or qualitative abnormalities of mitochondrial DNA, such as Alpers disease (AHS), childhood myocerebrohepatopathy spectrum (MCHS), myoclonic epilepsy myopathy sensory ataxia (MEMSA), spinocerebellar ataxia with epilepsy (SCAE), ataxia with neuropathy syndromes including MIRAS and SANDO, autosomal recessive progressive external ophthalmoplegia (arPEO), autosomal dominant progressive external ophthalmoplegia (adPEO), mitochondrial neurogastrointestinal encephalopathy (MNGIE), Pearson syndrome, Kearns-Sayre syndrome, infantile myopathy and spinal muscular atrophy relating to TK2 mutations, liver failure with depletion of mtDNA, pathologies associated with mutations of the genes SUCLA2 and SUCLAG1, RRM2B, AIF1, MPV17, or of diseases associated with point mutations of mitochondrial DNA, such as Leber hereditary optic neuropathy, MELAS syndrome, MERRF syndrome, and some forms of Leigh syndrome, chronic progressive external ophthalmoplegia, myopathy, cardiomyopathy, diabetes-deafness, encephalomyopathy, and deafness.

In an especial embodiment, the invention relates to a compound as defined above, for use in the treatment or prevention of diseases relating to at least one mutation, or at least one deletion or at least one insertion, or a combination thereof, in the POLG gene, said diseases including Alpers disease (AHS), childhood myocerebrohepatopathy spectrum (MCHS), myoclonic epilepsy myopathy sensory ataxia (MEMSA), spinocerebellar ataxia with epilepsy (SCAE), ataxia with neuropathy syndromes including MIRAS and SANDO, autosomal recessive progressive external ophthalmoplegia (arPEO) and autosomal dominant progressive external ophthalmoplegia (adPEO).

In another especial embodiment, the invention relates to a compound as defined above, for use in the treatment or prevention of diseases relating to a depletion or deletion of mitochondrial DNA, said diseases comprising autosomal recessive progressive external ophthalmoplegia, mitochondrial neurogastrointestinal encephalopathy, Pearson syndrome, Kearns-Sayre syndrome, infantile myopathy and spinal muscular atrophy relating to TK2 mutations, liver failure with depletion of mtDNA, pathologies associated with mutations of the genes SUCLA2 and SUCLAG1, RRM2B, AIF1, MPV17, and autosomal dominant progressive external ophthalmoplegia.

In another especial embodiment, the invention relates to a compound as defined above, for use in the treatment or prevention of diseases associated with a point mutation of mitochondrial DNA, said diseases including Leber optic neuropathy, MELAS syndrome, MERRF syndrome, and some forms of Leigh syndrome, chronic progressive external ophthalmoplegia, myopathy, cardiomyopathy, diabetes-deafness, encephalomyopathy, and deafness.

In an even more especial embodiment, the invention relates to a compound as defined above, for use in the treatment or prevention of MELAS syndrome.

MELAS syndrome (Mitochondrial Encephalopathy Lactic Acidosis Stroke) is a mitochondropathy due most frequently to a A3243 G mutation in the RNAt$^{Leu}$ of mitochondrial DNA. The disease usually begins in childhood or in young adults. In subjects suffering from this syndrome, there are often chronic symptoms such as cardiomyopathy, deafness, diabetes, short stature, muscle weakness, mental retardation, and disorders affecting learning, memory and/or attention span. For the most severe forms of MELAS, repeated vascular accidents are also responsible for serious neurological damage. Patients suffering from MELAS syndrome have hyperlactacidaemia in their blood, that is to say an increase in lactate, due to mitochondrial dysfunction and the resultant energy deficiency. In individuals suffering from MELAS syndrome a significant reduction of the activity of complex I, which is the first enzyme in the mitochondrial respiratory chain, is also observed. It is thus expected that a drug effective in the treatment of MELAS syndrome will increase the activity of complex I and reduce lactate production (by increasing energy production) in the patient.

DESCRIPTION OF THE FIGURES

FIG. 1 shows the optical density ($DO_{600}$) of a cell culture of mutant *Saccharomyces cerevisiae* yeast in the MIP1 gene (mip1$^{G651S}$) after 24 hours of culture as a function of the concentration of clofilium tosylate added to the culture medium.

FIG. 2 shows the frequency, as a percentage, of the production of small colonies of the mip1$^{G651S}$ yeast strain in the presence (CLOF) and absence (DMSO) of 32 µM clofilium tosylate in the culture medium.

FIG. 4 shows the number of colonies resistant to erythromycin ($Ery^R$) from the total number of colonies (frequency of cells resistant to erythromycin) of the recessive mip1 mutants in the absence (DMSO) and presence (CLOF) of 32 µM clofilium tosylate.

FIG. 5 shows the frequency, as a percentage, of production of small colonies, in the mip1$^{G651S}$, mip1$^{G651S}$, Δsml1, mip1$^{A692T}$ and mip1$^{A692T}$ Δsml1 yeast strains, in the presence of 32 µM clofilium tosylate (dark grey) or in the absence of clofilium tosylate (presence of DMSO, light grey).

FIG. 6 shows the speed of dioxygen consumption ($VO_2$) in nmol/2×10$^6$ cells/min in the yeasts expressing the wild-type MIP1 gene or the mutated mip1$^{G651S}$ gene, in the presence (CLOF) or in the absence (DMSO) of 32 µM clofilium tosylate.

FIG. 7 shows the analysis by SDS/PAGE gel electrophoresis of mitochondrial protein fractions of yeast cells grown in the presence (CLOF, +) or in the absence (DMSO, −) of 32 µM clofilium tosylate. The proteins studied were the Mip1-HA protein, the Mip1G651S-HA protein (SDS/PAGE gel analysis (6%)), the mitochondrial Cox2 protein and porin (SDS/PAGE gel analysis 10%). The proteins, after separation, were transferred to nitrocellulose membrane and were revealed by detecting the peroxidase activity (ECL$^{Plus}$) with the aid of primary antibodies and secondary antibodies coupled to horseradish peroxidase (HRP). The band marked with * is a non-specific reaction of anti-HA antibodies.

FIG. 8 shows the percentage of *Caenorhabditis elegans* nematode at stages L1 to L3 and at L4 adulthood stage relative to the total number of nematodes in a wild-type line (N2) and in a mutated TB2143 line (polg-1 (ok1458Δ/+)) carrying a heterozygous deletion of 2149 bp in the sequence encoding the polg-1 gene, as a function of the concentration of clofilium tosylate contained in the culture medium of the nematodes (NGM dishes).

FIG. 9 shows the percentage of increased haploinsufficient TB2143 nematode larvae (polg-1(ok1458Δ/+)) on NGM dishes containing 30 μg/mL ethidium bromide, the development of which stopped at stage L3 depending on the absence (DMSO) or presence (CLOF) of 50 μM clofilium tosylate on the dishes.

FIG. 10 shows the dose-response curve of clofilium tosylate for the resistance of haploinsufficient TB2143 nematodes (polg-1(ok1458Δ/+)) to ethidium bromide: the percentage of L3 larvae (halted development) is plotted against the concentration of clofilium tosylate contained in the NGM dishes of the nematodes comprising 30 μg/mL ethidium bromide.

FIG. 11 shows the dose-response curve of quinidine for the resistance of haploinsufficient TB2143 nematodes (polg-1(ok1458Δ/+)) to ethidium bromide: the percentage of L3 larvae (halted development) is plotted against the concentration of quinidine contained in the NGM dishes of the nematodes comprising 30 μg/mL ethidium bromide.

FIG. 13 shows the percentage of dead homozygous TB2143 nematodes (polg-1(ok1458Δ/Δ)) having intestinal and/or gonad extrusion on the $7^{th}$ day of adulthood in the absence (DMSO) and presence (CLOF) of 50 μM clofilium tosylate.

FIG. 14 shows the percentage of mtDNA of homozygous TB2143 nematodes (polg-1(ok1458Δ/Δ)) relative to the N2 reference strain in the presence of DMSO and in the presence of 50 μM clofilium tosylate.

FIG. 15 shows the cell index, representative of the cell viability of human fibroblasts cultured with different concentrations of clofilium tosylate as a function of time.
Part A shows the cell index of control fibroblasts.
Part B shows the cell index of fibroblasts from a patient having a mutation on each allele of the POLG gene.

FIG. 16 shows the ratio of the amount of mtDNA to the amount of nuclear DNA (nuDNA) in control fibroblasts and fibroblasts from a patient with a mutation on each allele of the POLG gene cultured in the absence (DMSO) and presence (CLOF) of clofilium tosylate 2.5 μM.

FIG. 17 shows the percentage of depletion of mtDNA of skin fibroblasts from a patient with a mutation on each allele of the POLG gene compared to the amount of mtDNA of control skin fibroblasts, grown in a quiescent environment in the absence of any treatment (NT) or in the presence of DMSO (DMSO) or of 1 μM clofilium tosylate (CLOF) as a function of time.

FIG. 18 shows the percentage of haploinsufficient TB2143 nematodes (polg-1(ok1458Δ/+)) at adulthood stage and at development stage L4 after 4 days of culture on NGM dishes supplemented with 30 μg/mL ethidium bromide and various concentrations of clofilium tosylate or DMSO.

FIG. 19 shows the percentage of haploinsufficient TB2143 nematodes (polg-1(ok1458Δ/+)) at adulthood stage and at development stage L4 after 4 days of culture on NGM dishes supplemented with 30 μg/mL of ethidium bromide and different concentrations of ibutilide hemifumarate or DMSO.

FIG. 20 shows the percentage of haploinsufficient TB2143 nematodes (polg-1(ok1458Δ/+)) at adulthood stage and at development stage L4 after 4 days of culture on NGM dishes supplemented with 30 μg/mL of ethidium bromide and 50 μM clofilium tosylate, or different concentrations of dofetilide or DMSO.

FIG. 22 shows the effect of clofilium tosylate on the ratio of complex I/citrate synthase activities and lactate production of neuronal cybrids derived from a MELAS patient (m.3243 A>G tRNA$^{leu}$ mutation).
Part A shows the ratio of complex I/citrate synthase activities, as a percentage compared to the control, after treatment of the neuronal cybrids with DMSO (control) or 300 nM (CT 300 nM) of clofilium tosylate, after 48 hours of treatment. N=4. CS=citrate synthase.
Part B shows the lactate production, as a percentage relative to the control, by the neuronal cybrids after treatment of the neuronal cybrids with DMSO (control) or 300 nM (CT 300 nM) of clofilium tosylate for 48 hours. N=4.

FIG. 23 shows the dose-response of ibutilide for the ratio of complex I/citrate synthase activities and lactate production of neuronal cybrids derived from a MELAS patient (m.3243A>G tRNA$^{leu}$ mutation).
Part A shows the ratio of complex I/citrate synthase activities, as a percentage compared to the control, after treatment of the neuronal cybrids with DMSO (control) or 1 μM (ibu 1 μM) or 300 nM (ibu 300 nM) of ibutilide for 48 hours. N=4. CS=citrate synthase.
Part B shows the lactate production, as a percentage relative to the control, by the neuronal cybrids after treatment of the neuronal cybrids with DMSO (control) or 1 μM (ibu 1 μM) or 300 nM (ibu 300 nM) of ibutilide over 48 hours. N=4.

FIG. 24 shows the analysis by SDS/PAGE gel electrophoresis of the protein fractions of total extracts of control fibroblasts (control) and fibroblasts from a patient with a mutation on each allele of the POLG gene (patient) in cell growth conditions. The fibroblasts are cultured in the presence of DMSO 0.1% (D) or with 0.5 μM or 1.0 μM of clofilium tosylate (CLO). The proteins studied are the POLG protein (SDS/PAGE gel analysis (6%)), ATP5B and TFAM mitochondrial proteins, as well as TUB3A cytosolic protein as batch control.

FIG. 25 shows the percentage of the increase in the number of mtDNA copies of skin fibroblasts from a patient with a mutation on each allele of the POLG gene compared to the number of mtDNA copies of untreated fibroblasts from the patient (DMSO), cultured in quiescent medium in the presence of DMSO (DMSO) or in the presence of different concentrations of clofilium tosylate: 0.5 µM (CLO 0.5), 1 µM (CLO 1), 2.5 µM (CLO 2.5), as a function of the number of days of treatment (18-day treatment).

EXAMPLES

Figure 1:
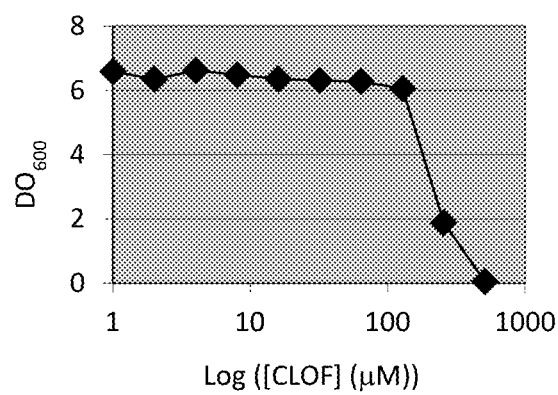
FIG. 1.

Examples 1 to 14, 17 to 22 and 24 to 25 concern clofilium tosylate: examples 1 to 6 and 17 concern the yeast *Saccharomyces cerevisiae*, examples 7 to 11 and 20 concern the nematode *Caenorhabditis elegans*, examples 12 to 14, 18, 19, 24 and 25 concern human fibroblasts, and example 22 concerns neuronal cybrids derived from a MELAS patient (m.3243A>G tRNA$^{leu}$ mutation). Example 21 concerns the combination of clofilium tosylate with resveratrol and human fibroblasts.

Example 15 concerns ibutilide and the nematode, example 23 concerns ibutilide and the neuronal cybrids derived from a MELAS patient (m.3243A>G tRNA$^{leu}$ mutation), example 16 concerns dofetilide and the nematode.
Material and Methods The *S. cerevisiae* yeasts used in examples 1 to 6 and 17 are yeasts of DWM-5A genetic background: Mat a de2-1 leu-3, 112 ura3-1 trp1-1 his3-11, 15 can1-100 Δmip1::KanR transformed by a single-copy plasmid (ARS-CEN) pFL39 (TRP1) allowing the expression of different alleles of MIP1 (Baruffini, E., Lodi, T., Dallabona, C., Puglisi, A., Zeviani, M. and Ferrero, I. (2006) Genetic and Chemical rescue of the *Saccharomyces cerevisiae* phenotype induced by mitochondrial DNA polymerase mutations associated with progressive external ophthalmoplegia in humans. *Hum. Mol. Genet.*, 15, 2846-2855).

The *C. elegans* nematodes used in examples 7 to 11 and 15, 16 and 20 are the wild-type BRISTOL N2 line, the VC1224 line (polg-1(ok1458)/mT1 II; +/mT1[dpy-10 (e128)] II) from the Caenorhabditis Genetics Center (CGC) consortium, the TB2143 line (polg-1(ok1458)/+II; +/mln [dpy-10(e128) mlsl4] II) (A. Trifunovic, Germany) and the DA631 line (eat-3(ad426) II; him-8(el489) IV) (CGC).

Example 1: Determination of the Maximum Concentration of Clofilium Tosylate Tolerated by the *Saccharomyces Cerevisiae* Mip1$^{G651S}$ Yeast Strain The inhibition of growth (MIC Minimum Inhibitory Concentration) of clofilium tosylate on the mip1$^{G651s}$ strain was tested for concentrations of clofilium tosylate of 512 µM, 256 µM, 128 µM, 64 µM, 32 µM, 16 µM, 8 µM, 4 µM, 2 µM, and 1 µM.

From o/n pre-culture in selective medium (SC-URA, 2% ethanol (v/v)), 50 mL of rich YPD medium (1% Yeast Extract, 0.5% Bacto Peptone, 2% Glucose) were seeded at a DO$_{600}$ of 0.05/mL. The 50 mL of culture were distributed in a series of ten tubes on the basis of 2 mL of culture/tube, with 4 mL of culture being placed in the last tube. Clofilium tosylate was added to this last tube (tube 1) at the maximum concentration: 512 µM (maximum solubility). From this tube (tube 1), 2 mL of culture were placed into tube 2. Tube 2 contained 4 ml of culture and clofilium tosylate at a concentration of 256 µM. 2 mL of tube 2 were added to tube 3, and so on. Each tube contained the drug at a concentration equal to half that of the previous tube. Two controls were provided—without clofilium tosylate and with DMSO (the volume being the same as that used to dilute the clofilium tosylate). The cultures were incubated at 28° C. with stirring for 24 hours, and the optical density (DO$_{600}$) was measured.

The results are shown in FIG. 1.

The concentration of clofilium tosylate chosen for the study of its effect in the *S. cerevisiae* yeast was 32 µM.

Example 2: Effect of Clofilium Tosylate on the Production of Small Colonies in Mutated Mip1 Yeast Strains The rate of small cells in a population represents the cells not breathing due to rearrangements of the mtDNA and/or having lost their mtDNA.
2.1. Procedure From a pre-culture in selective medium (SC-TRP, 2% ethanol (v/v)) of the mutated mip1 strain, 2.10$^5$ cells/mL were seeded in 2 mL of rich YPD medium (1% Yeast Extract, 0.5% Bacto Peptone, 2% Glucose) in the presence of 32 µM clofilium tosylate or DMSO. The cells were then incubated at 28° C. for two cycles of 24 hours. The cells were then diluted to have about 200 to 250 cells per dish and spread on differential synthetic medium (SC-TRP, 0.3% glucose, 2% ethanol). The number of small colonies was calculated after 6 days of incubation at 28° C. (Baruffini, E., Lodi, T., Dallabona, C., Puglisi, A., Zeviani, M. and Ferrero, I. (2006) Genetic and Chemical rescue of the *Saccharomyces cerevisiae* phenotype induced by mitochondrial DNA polymerase mutations associated with progressive external ophthalmoplegia in humans. *Hum. Mol. Genet.*, 15, 2846-2855).
2.2. Effect of Clofilium Tosylate on the Production of Small Colonies of the Mutant Mip1$^{G651S}$ Yeast Strain The effect of the clofilium tosylate on the production of small colonies was measured in the mutant mip1$^{G651S}$ yeast.

Figure 2:
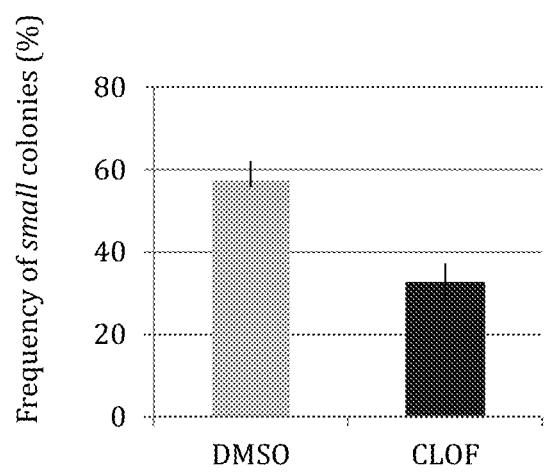
FIG. 2.

The results are shown in FIG. 2.

Figure 3:
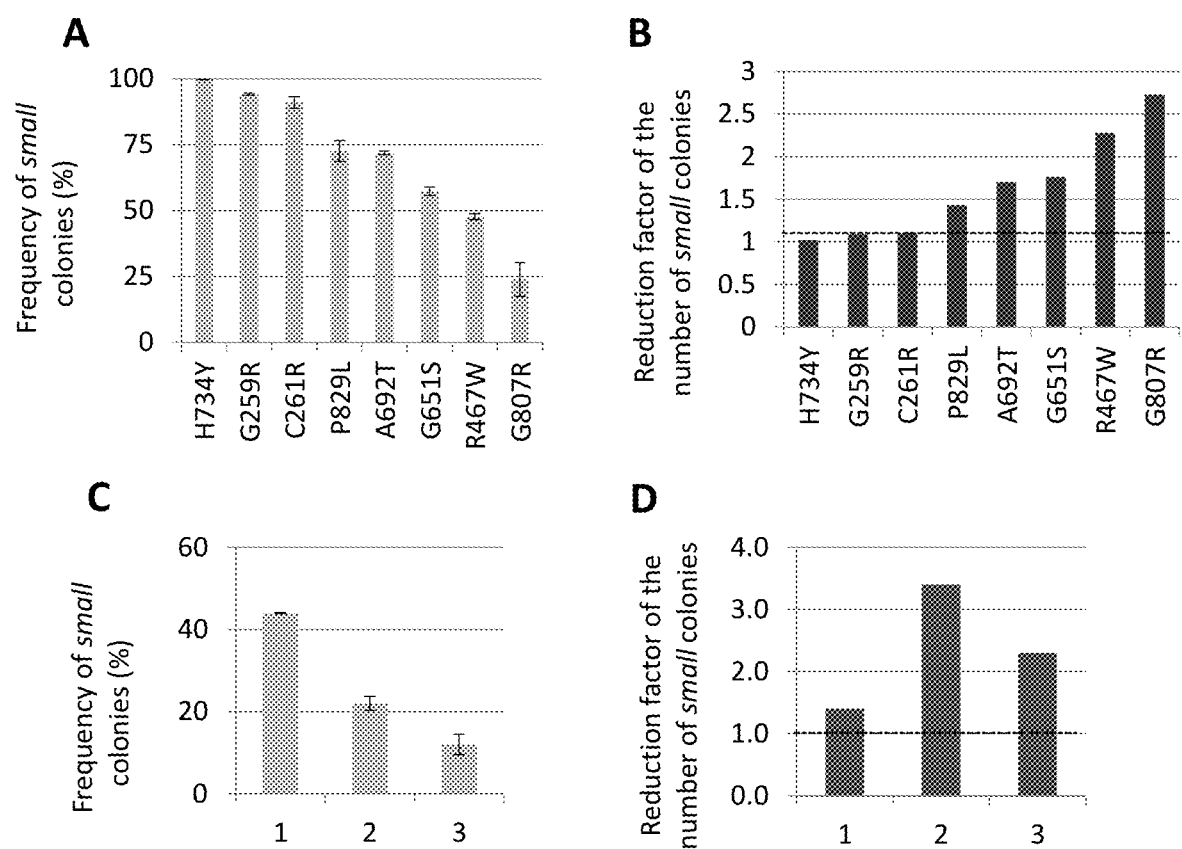
FIG. 3: Part A shows the frequency, as a percentage, of production of small colonies of the recessive mip1 mutants. Part B shows the reduction in the number of small colonies in the presence of 32 µM clofilium tosylate compared to the number of untreated cells (cells in the presence of DMSO) in the recessive mip1 mutants.
Part C shows the frequency, as a percentage, of production of small colonies of the dominant mip1 mutants.
Part D shows the reduction in the number of small colonies in the presence of 32 µM clofilium tosylate compared to the number of untreated cells (cells in the presence of DMSO) in the dominant mip1 mutants.

Clofilium tosylate reduced the production of small colonies of the mutant mip1$^{G651S}$ yeast 1 strain.
2.3. Effect of Clofilium Tosylate on the Production of Small Colonies in Different Recessive and Dominant Mutants of Mip1 in the Yeast The effect of the clofilium tosylate on the production of small colonies was measured in 8 recessive mip1 mutants:

| | |
|---|---|
| H734Y | A692T |
| (mutated domain: polymerase) | (mutated domain: polymerase) |
| G259R | G651S |
| (mutated domain: exonuclease) | (mutated domain: polymerase) |
| C261R | R467W |
| (mutated domain: exonuclease) | (mutated domain: linker) |
| P829L | G807R |
| (mutated domain: polymerase) | (mutated domain: polymerase) | an in 3 dominant mip1 mutants:
Y757C (mutated domain: polymerase)
K749R (mutated domain: polymerase)
E698G (mutated domain: polymerase)
The results are shown in FIG. 3.

Clofilium tosylate reduced the production of cells not breathing, irrespective of the mutated MIP1 domain (exonuclease, polymerase or linker), with the exception of mutations producing more than 90% of small colonies.

Example 3: Effect of Clofilium Tosylate on the Fidelity of the Different MIP1 Mutants in the Yeast A disruption of the fidelity of the Mip1 mitochondrial polymerase can be evaluated by measuring the frequency of cells resistant to erythromycin ($Ery^R$). The $Ery^R$ mutations are caused by mutations in the 21S mitochondrial ribosomal RNA encoded by mtDNA that may occur after incorporation of a bad nucleotide (Baruffini, E., Lodi, T., Dallabona, C., Puglisi, A., Zeviani, M. and Ferrero, I. (2006) Genetic and Chemical rescue of the Saccharomyces cerevisiae phenotype induced by mitochondrial DNA polymerase mutations associated with progressive external ophthalmoplegia in humans. Hum. Mol. Genet., 15, 2846-2855). Measuring the resistance to erythromycin is one way to directly measure the point mutations of mtDNA.

Independent colonies were seeded in 10 mL of minimal medium (SC-TRP, 2% glucose) in the presence of 32 µM clofilium tosylate or DMSO to stationary phase. To determine the total number of cells capable of breathing, an aliquot of each culture was spread on rich YPE medium (1% Yeast Extract, 0.5% Bacto Peptone, 2% Ethanol). The remaining cultures were spread on N1 medium containing 2.5 mg/mL of erythromycin (2% peptone, 1% yeast extract, 40 mg/L adenine, 3% ethanol, 3% glycerol in 25 mM phosphate buffer pH 6.5, and supplemented with 2.5 g/L of erythromycin (SIGMA)) and incubated at 28° C. for 8 days. The experiment was performed in duplicate. The mutation frequency was calculated as the number of $Ery^R$ colonies among the total number of colonies (Baruffini, E., Lodi, T., Dallabona, C., Puglisi, A., Zeviani, M. and Ferrero, I. (2006) Genetic and Chemical rescue of the Saccharomyces cerevisiae phenotype induced by mitochondrial DNA polymerase mutations associated with progressive external ophthalmoplegia in humans. Hum. Mol. Genet., 15, 2846-2855).

Figure 4:
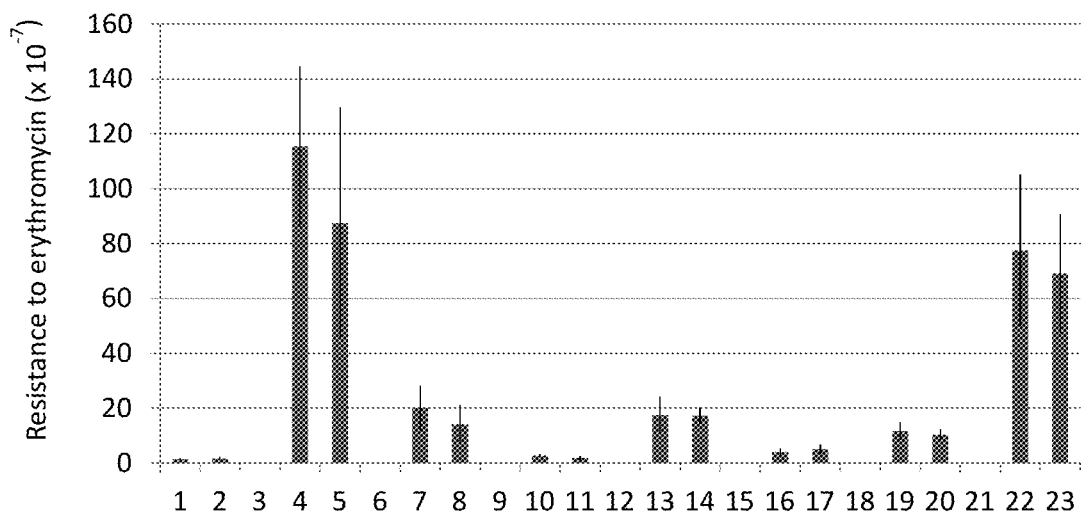
FIG. 4.

The results are shown in FIG. 4.

Clofilium tosylate had no effect on the fidelity of the different MIP1 yeast mutants.

Example 4: Effect of Clofilium Tosylate and Availability of dNTPs on the Stability of the mtDNA of the $Mip1^{G651S}$ and $Mip1^{A692T}$ Yeast Mutants Deletion of the SML1 gene encoding the inhibitor of RNRI (ribonucleotide diphosphate reductase, enzyme limiting the synthesis pathway of dNTPs) is known to be a genetic suppressor of the instability of the mtDNA caused by mutations in the MIP1 gene (Wang P J, Chabes A, Casagrande R, Tian X C, Thelander L and Huffaker T C. (1997) Rnr4p a novel ribonucleotide reductase small-subunit protein. Mol Cell Biol, 17, 6114-6121).

The frequency of the small colonies was determined for the $mip1^{G651S}$ and $mip1^{A692T}$ strains, whether deleted or not from the SML1 gene and in the presence of 32 µM clofilium tosylate or DMSO.

From pre-cultures in selective medium (SC-TRP, 2% ethanol (v/v)) of mutated mip1 strains, $2.10^5$ cells/mL were seeded in 2 mL of rich YPD medium in the presence of 32 µM clofilium tosylate or DMSO, then incubated at 28° C. for 24 hours. The cells were then diluted to have about 200 to 250 cells per dish and were spread on differential synthetic medium (SC-TRP, 0.3% glucose, 2% ethanol). The number of small colonies was calculated after 5 days of incubation at 28° C.

Figure 5:
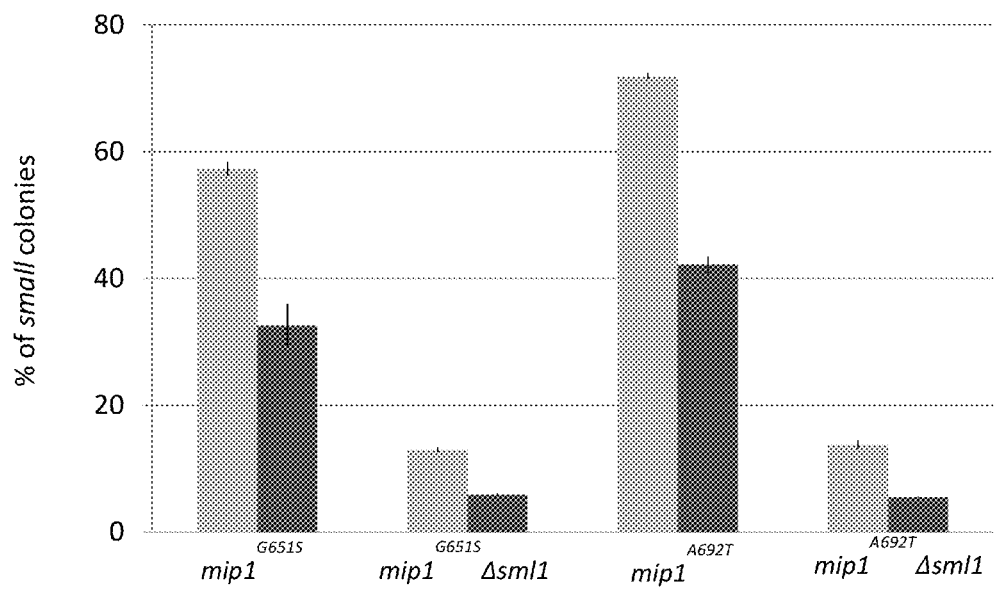
FIG. 5.

The results are shown in FIG. 5.

Clofilium tosylate and the availability of dNTPs (caused by the deletion of the SML1 gene) had an additive effect on the stability of the mtDNA of the $mip1^{G651S}$ and $mip1^{A692T}$ yeast mutants.

Example 5: Effect of Clofilium Tosylate on the Respiration of Yeast Cells

The respiration rate is the amount of oxygen consumed per unit of time and biological material. It reflects the activity of the oxidative metabolism of the cells.

Oxygen consumption was measured on whole cells using a HANSATECH electrode. The yeast cells expressing the wild-type MIP1 gene or the mutated $mip1^{G651S}$ gene were cultured for 7-8 generations in a YPE medium (1% Yeast Extract, 0.5% Bacto Peptone, 2% Ethanol) supplemented with DMSO or 32 µM clofilium tosylate at 28° C. with stirring. A volume corresponding to a total of 60 units of $DO_{600}$ of each culture was centrifuged for 5 min at 3000 g. The pellet was resuspended in YPE in order to have $6.10^5$ cells/µl. 50 µL, that is to say $3.10^7$ cells, were introduced into the measuring chamber of the HANSATECH electrode, which was maintained at 28° C. The $O_2$ consumption was observed and recorded in real time. The $O_2$ consumption rate was calculated from the linear part of the $O_2$ consumption curve.

Figure 6:
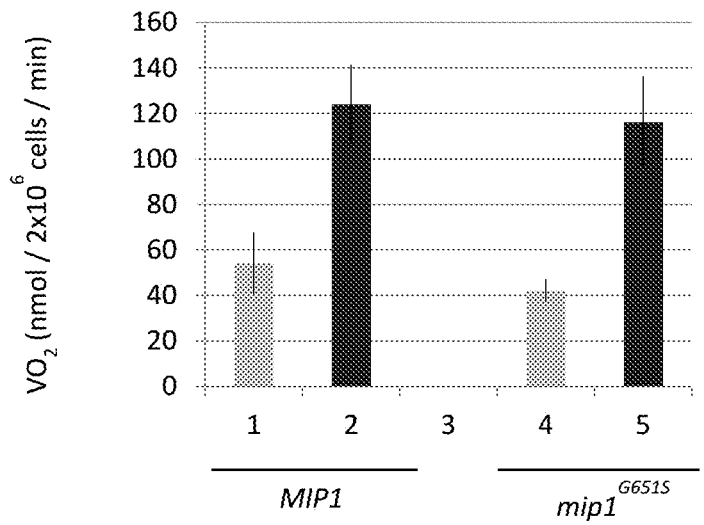
FIG. 6.

The results are shown in FIG. 6.

The yeast cells treated by clofilium tosylate breathed better.

Example 6: Effect of Clofilium Tosylate on the Amount of Wild-type Mip1 Yeast Proteins or Mutated Mip1G651S Yeast Proteins The analysis of the effect of clofilium tosylate on the amount of wild-type or mutated Mip1 proteins was carried out on cell extracts enriched in mitochondria. In order to visualise the expression of the Mip1 and Mip1G651S proteins, the sequence encoding three HA epitopes was cloned in 3' and in phase with the coding sequence of Mip1 and Mip1G651S.

The yeast cells were cultured in selective medium (SC-TRP, 2% ethanol) overnight. Then, the cells were seeded at an initial optical density ($DO_{600}$) of 0.05 in 100 mL of YPE (1% Yeast Extract, 0.5% Bacto Peptone, 2% Ethanol) supplemented either by DMSO or by 32 µM clofilium tosylate at 28° C. with stirring until a $DO_{600}$ between 3 and 4 was achieved. The cells were centrifuged at 3000 g for 5 min and washed with water. The isolation of the fraction enriched in mitochondria and protein extraction of this fraction were carried out according to the protocol described by Hoffman et al., 2009 (Hofmann, L., Saunier, R., Cossard, R., Esposito, M., Rinaldi, T. and Delahodde, A. (2009) A non-proteolytic proteasome activity controls organelle fission in yeast. J. Cell. Sci., 122, 3673-3682).

The protein extracts of the fractions enriched in mitochondria were analysed by SDS/PAGE gel electrophoresis (6% for the analysis of the proteins Mip1-HA and Mip1G651S-HA and 10% for the analysis of Cox2 mitochondrial proteins (encoded by mtDNA) and porin). After separation over polyacrylamide gel, the proteins were transferred to a nitrocellulose membrane. After saturation of the membranes by 5% (w/v) skimmed milk solution, the membranes were incubated for one hour under stirring in the presence of the corresponding primary antibodies (the protein Mip1: anti-HA diluted to $1/5000^{th}$, the protein Cox2: anti-Cox2 diluted to $1/500^{th}$, porin: anti-porin diluted to $1/25000^{th}$). After washing in TBS buffer, the membranes were incubated for one hour in the presence of secondary antibodies coupled to horseradish peroxidase (HRP) diluted to $1/5000^{th}$. The membranes were then washed again in TBS buffer. The proteins were then revealed with the aid of the ECL$^{Plus}$ kit for detecting peroxidase activity obtainable from GE Healthcare.

Figure 7:
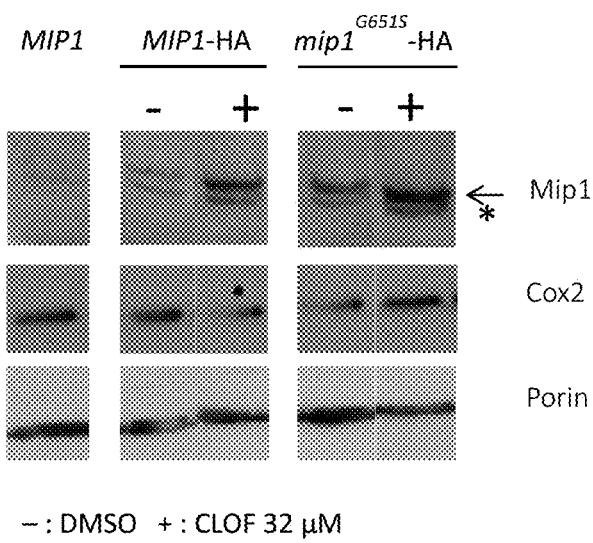
FIG. 7.

The results are shown in FIG. 7.

The amount of wild-type Mip1 or mutated Mip1G651S yeast protein was increased in the presence of clofilium tosylate.

Example 7: Determination of the Non-toxic Concentration of Clofilium Tosylate (MIC, Minimum Inhibitory Concentration) in the *Caenorhabditis Elegans* Nematode A series of NGM dishes containing clofilium tosylate at concentrations of 1 µM, 5 µM, 10 µM, 50 µM, 100 µM or 200 µM were prepared (three dishes for each concentration). Between 30 and 40 synchronised L1 larvae of the wild-type N2 BRISTOL line or mutated VC1224 line (polg-1 (ok1458Δ/+)/mT1 II; +/mT1 [dpy-10(e128)] II), these being nematodes carrying a heterozygous deletion of 2149 bp in the sequence encoding the polg-1 gene, were deposited on each of these dishes. Their development was observed for 4 days.

Figure 8:
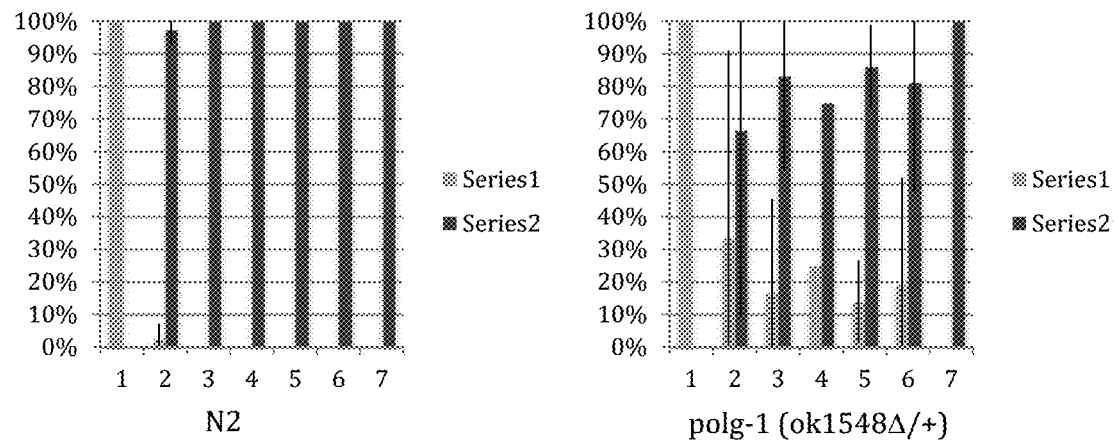
FIG. 8.

The results are shown in FIG. 8.

For the wild-type line, a halt in the development at stage L3 or a slowdown in development was observed at 100 µM of clofilium tosylate, indicating that the maximum concentration to use is 50 µM. For the polg-1(ok1458Δ/+) strain, the larvae developed similarly to concentrations ranging from 1 µM to 50 µM of clofilium tosylate, The concentration of clofilium tosylate chosen for future experiments with the nematode was 50 µM.

Example 8: Effect of Clofilium Tosylate on the Resistance of Haploinsufficient polg-1 Nematodes (polg-1(ok1548Δ/+)) to Ethidium Bromide Ethidium bromide is an intercalating agent of DNA, especially of mtDNA, rich in adenine and thymidine. At high concentrations it halts the development of the worms at stage L3 (Addo, M. G., Cossard, R., Pichard, D., Obiri-Danso, K., Rötig, A. and Delahodde, A. (2010) *Caenorhabditis elegans*, a pluricellular model organism to screen new genes involved in mitochondrial genome maintenance. *BBA-Mol. Basis Dis.*, 1802, 765-773. The haploinsufficient TB2143 nematodes (polg-1(ok1458Δ/+)) are highly sensitive to low doses of ethidium bromide (30 µg/mL) with 90% of the larvae halted at stage L3.

8.1. Test for Resistance to Ethidium Bromide

Around thirty wild-type larvae or larvae mutated in polg-1 (TB2143 line (polg-1(ok1458Δ/+))) synchronised at stage L1 were deposited on NGM dishes containing 30 µg mL L1 ethidium bromide and either DMSO or 50 µM clofilium tosylate (experiment performed in triplicate). Larval development was examined after 4 days of treatment.

Figure 9:
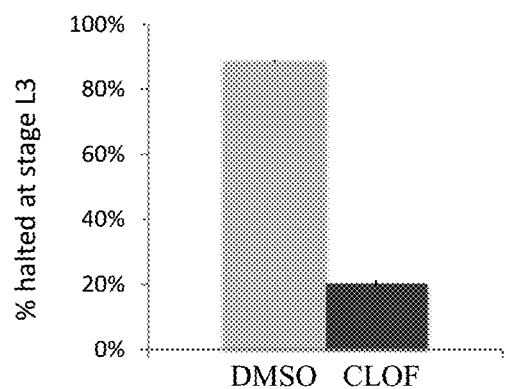
FIG. 9.

The results are shown in FIG. 9.

Clofilium tosylate provided increased resistance of the haploinsufficient polg-1(ok1548Δ/+) nematodes to ethidium bromide.

8.2. Dose-Response of Clofilium Tosylate for the Resistance of Haploinsufficient Polg-1(ok1548Δ/+) Nematodes to Ethidium Bromide Around thirty larvae mutated in polg-1 and synchronised at stage L1, TB2143 line (polg-1(ok1548Δ/+)), were deposited on NGM dishes containing 30 µg/ml ethidium bromide and either DMSO or different concentrations of clofilium tosylate: 1 µM, 5 µM, 10 µM and 50 µM (experiment performed in triplicate). Larval development was examined after 4 days of treatment.

Figure 10:
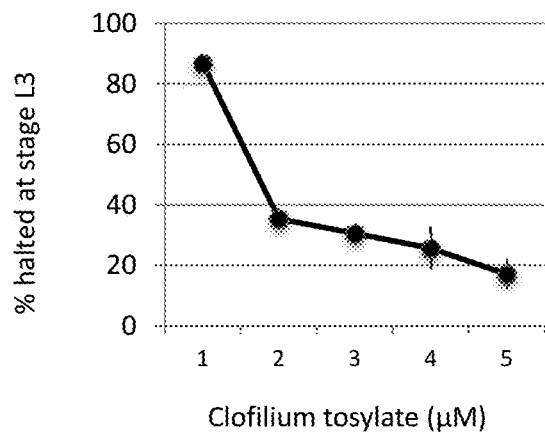
FIG. 10.

The dose-response curve is given in FIG. 10.

The dose-response of clofilium tosylate was determined once again in accordance with the same procedure, with the following concentrations of clofilium tosylate: 0.1 µM, 0.5 µM, 1 µM, 5 µM, 10 µM and 50 µM.

Figure 18:
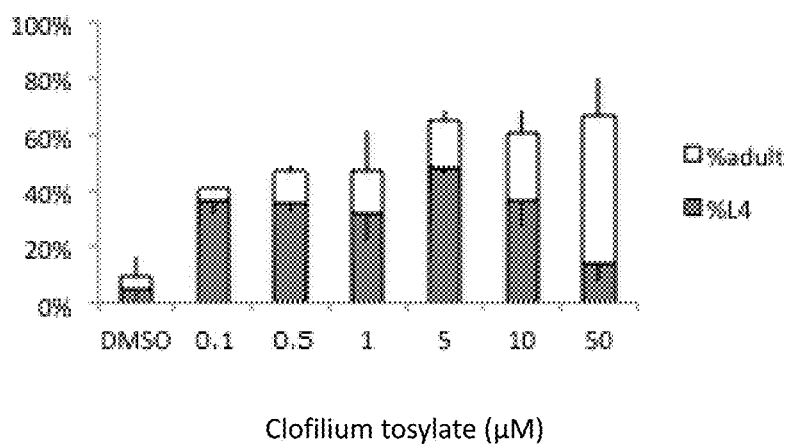
FIG. 18.

The results are shown in FIG. 18.

8.3. Dose-Response of Quinidine (Negative Control), for the Resistance of Haploinsufficient Polg-1(Ok1548Δ/+) Nematodes to Ethidium Bromide Around thirty larvae mutated in polg-1 and synchronised at stage L1, TB2143 line (polg-1(ok1548Δ/+)), were deposited on NGM dishes containing 30 µg/ml ethidium bromide and either DMSO or different concentrations of quinidine, a class I antiarrhythmic agent: 10 µM, 30 µM, 100 µM and 300 µM (experiment performed in triplicate). Larval development was examined after 4 days of treatment.

Figure 11:
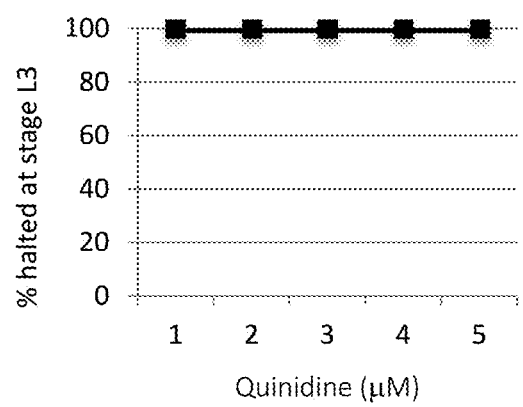
FIG. 11.

The dose-response curve is given in FIG. 11.

Example 9: Effect of Clofilium Tosylate on the Number of Laid and Hatched Eggs of Homozygous TB2143 Nematodes (polg-1(Δ/Δ))

Four homozygous TB2143 larvae (polg-1(ok1548Δ/Δ)) at stage L4 were deposited on each NGM dish containing either DMSO or 50 µM clofilium tosylate (three dishes for each treatment group). They were incubated at 20° C. to adulthood stage. The adults were moved every 9 to 12 hours, over 6 to 7 days, to new dishes containing DMSO or 50 µM clofilium tosylate until there were no eggs in the uterus, and the number of laid eggs was counted. Each laying process was monitored until the following day in order to count the hatching.

Figure 12:
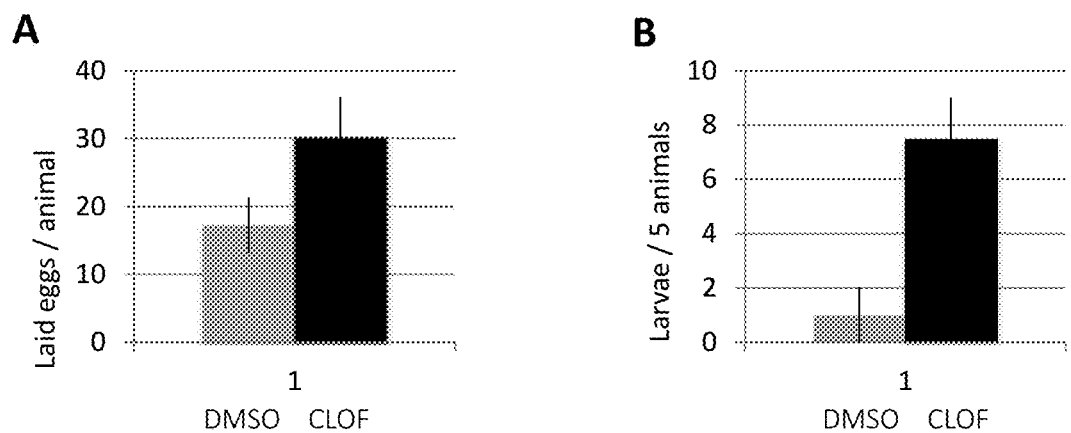
FIG. 12: Part A shows the number of eggs laid by homozygous TB2143 nematodes (polg-1(Δ/Δ)) in the absence (DMSO) or in the presence (CLOF) of 50 μM clofilium tosylate in the NGM dishes of the nematodes.
Part B shows the number of larvae, that is to say hatchings of the eggs laid, for 5 homozygous TB2143 nematodes (polg-1(Δ/Δ)) in the absence (DMSO) or presence (CLOF) of 50 μM clofilium tosylate in the NGM dishes of the nematodes.

The results are shown in FIG. 12.

Clofilium tosylate increased the number of laid eggs and the hatching of embryos of homozygous TB2143 nematodes (polg-1(Δ/Δ)).

Example 10: Effect of Clofilium Tosylate on Gonad Extrusion and/or Intestinal Extrusion of Homozygous Nematodes Ten homozygous TB2143 larvae (polg-1(ok1548Δ/Δ)) at stage L4 were deposited on each NGM dish containing either DMSO or 50 µM clofilium tosylate (three dishes for each treatment group) and incubated at 20° C. Their survival was monitored until the 7$^{th}$ day of adulthood. The number of dead animals, not responding to any stimulation, and having intestinal and/or gonad extrusion was counted. The few animals that died of dehydration at the edge of the petri dishes were excluded from the analysis.

Figure 13:
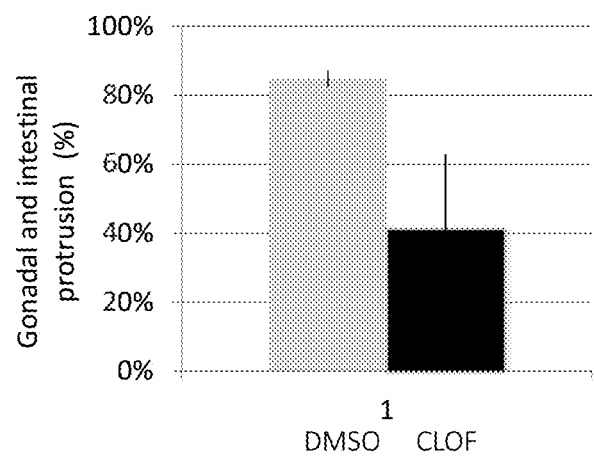
FIG. 13.

The results are shown in FIG. 13.

Clofilium tosylate reduced the premature death of homozygous nematodes by gonad and/or intestinal extrusion.

Example 11: Effect of Clofilium Tosylate on the Amount of mtDNA of Homozygous TB2143 Nematodes (polg-1(ok1548Δ/Δ)) Depleted of mtDNA Ten homozygous or wild-type TB2143 larvae (polg-1 (ok1548Δ/Δ)) at stage L4 were deposited on each NGM dish containing either DMSO or 50 µM clofilium tosylate (three dishes for each treatment group). They were incubated at 20°

C. until the 6$^{th}$ day of adulthood. Extraction of the total nematode DNAs was performed with the Nucleospin Kit Tissue kit (Macherey Nagel). The quantifications of mtDNA and nuclear DNA were performed as described in Addo et al., 2010 (Addo, M. G., Cossard, R., Pichard, D., Obiri-Danso, K., Rötig, A. and Delahodde, A. (2010) *Caenorhabditis elegans*, a pluricellular model organism to screen new genes involved in mitochondrial genome maintenance. *BBA-Mol. Basis Dis.*, 1802, 765-773).

Figure 14:
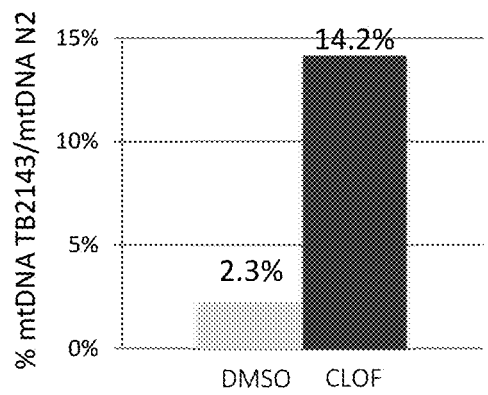
FIG. 14.

The results are shown in FIG. 14 and in Table 1.

TABLE 1

Ratio of the amount of mtDNA to the amount of nuclear DNA per wild-type N2 BRISTOL nematode treated with DMSO and per homozygous TB2143 nematode (polg-1(ok1548Δ/Δ)) treated either with DMSO or with 50 μM clofilium tosylate (CLOF).

| genotype | treatment | mtDNA/nuDNA |
|---|---|---|
| wild-type (N2) | DMSO | 488.9 |
| polg-1(ok1548Δ/Δ) | DMSO | 11.2 |
| polg-1(ok1548Δ/Δ) | CLOF | 69.2 |

Clofilium tosylate increased the amount of mtDNA of homozygous TB2143 nematodes (polg-1(ok1548Δ/Δ)) depleted of mtDNA.

Example 12: Determination of the Maximum Non-toxic Concentration of Clofilium Tosylate on Cultures of Control Fibroblasts and of Fibroblasts from a Patient with a Mutation on Each Allele of the POLG Gene Skin fibroblasts from the control and from the patient were cultured in DMEM Galactose (DMEM free of glucose (Life Technologies) supplemented with 10 mM galactose, 10% foetal bovine serum, 200 U/mL penicillin, 200 U/mL streptomycin). Uridine (50 μg/mL) and sodium pyruvate (2.5 mM) were added to the culture medium to maintain the cells expressing a deficiency of the respiratory chain. The cells were incubated in a controlled atmosphere at 37° C. and 5% $CO_2$.

Cell growth of patient and control fibroblasts was measured continuously for 140 h by use of an xCELLigence apparatus (ACEA Biosciences) in 96-well plates. The background noise of the signal was measured with 50 μL of culture medium per well. 50 μL of medium containing 1350 fibroblasts were then added to each well. The impedance measurement was taken every minute for 9 h and then every 15 minutes until the end of analysis.

Clofilium tosylate was diluted in 0.1% DMSO and used at different concentrations (2.5 μM, 5 μM, 10 μM) in a total volume of 50 μL. Toxic concentrations of clofilium tosylate were determined by adding the drug from the point of cell seeding. For each drug concentration and each control, the analysis was carried out in triplicate on 96-well plates. A mathematical algorithm was used to convert the impedance signal into cell index (CI). This index was proportional to the number of cells adhering to the bottom of the well and their form.

Figure 15:
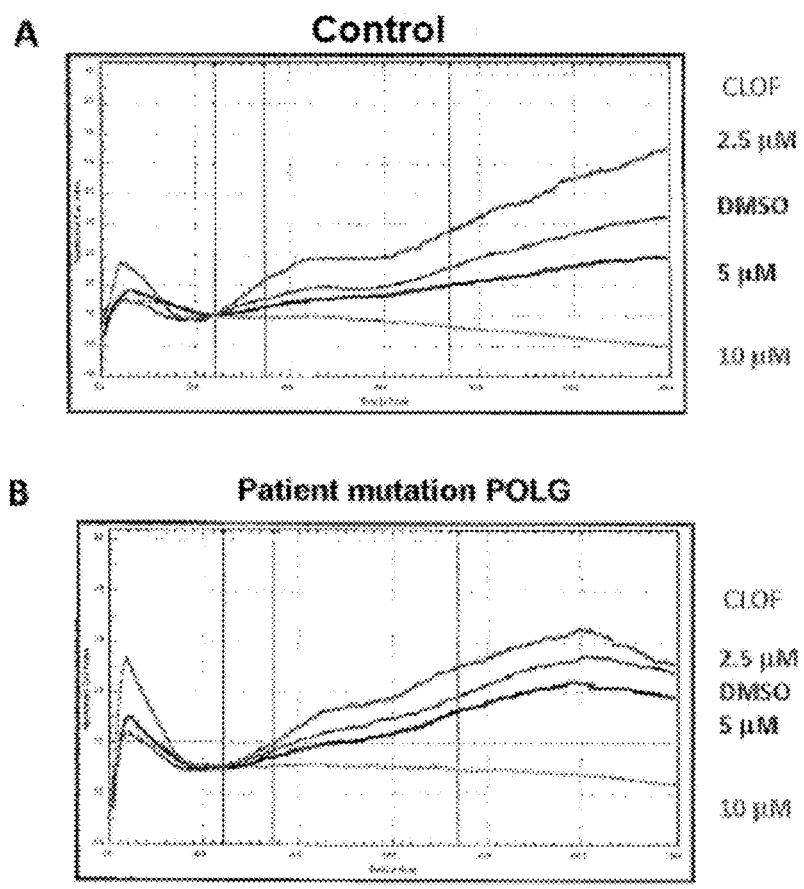
FIG. 15.

The results are shown in FIG. 15.

The maximum approved concentration of clofilium tosylate for cultures of control fibroblasts and of fibroblasts from a patient with a mutation on each allele of the POLG gene was 2.5 μM.

Example 13: Effect of Clofilium Tosylate on the Amount of mtDNA in the Fibroblasts from a Patient with a Mutation on Each Allele of the POLG Gene, Said Fibroblasts Having been Cultured in Cell Growth Conditions Skin fibroblasts from the control and from the patient were cultured to 100% confluence in a complete Dulbecco's Modified Eagle Medium (DMEM) high glucose medium (4.5 g/L of D-glucose, 110 mg/L sodium pyruvate, 10% foetal bovine serum, 1% penicillin/streptomycin from the stock solution containing 10,000 I.U. penicillin and 10,000 μg/mL streptomycin) at 37° C. under 5% $CO_2$. At confluence, the cultures were trypsinised and placed back in culture at 30% confluence in a complete DMEM high glucose medium supplemented with either 0.1% DMSO or with 2.5 μM clofilium tosylate. They were incubated at 37° C. under 5% $CO_2$ and harvested at 100% confluence. The total fibroblast DNAs were extracted by the phenol-chloroform method, and the mtDNA and nuclear DNA were quantified by qPCR as described in Sarzi et al., 2007 (Sarzi, E., Bourdon, A., Chrétien, D., Zarhrate, M., Corcos, J., Slama, A., Cormier-Daire, V., De Lonlay, P., Munnich, A. and Rötig, A. (2007) Mitochondrial DNA Depletion is a Prevalent Cause of Multiple Respiratory Chain Deficiency in Childhood. *J Pediatr,* 105, 531-534).

Figure 16:
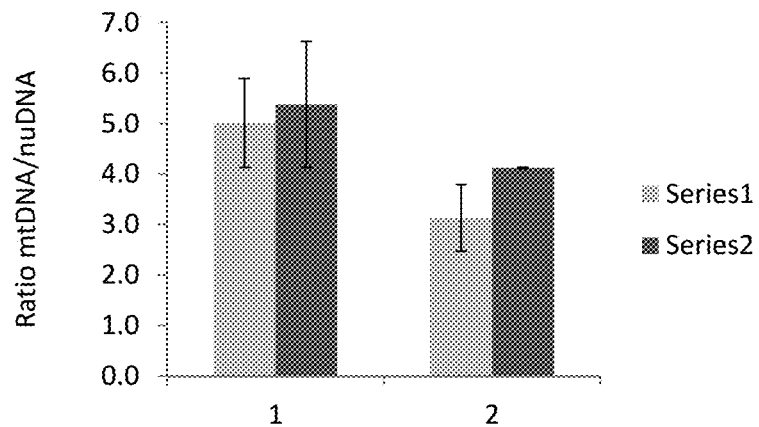
FIG. 16.

The results are shown in FIG. 16.

In cell growth conditions, clofilium tosylate slightly increased the amount of mtDNA in the fibroblasts from a patient with a mutation on each allele of the POLG gene.

The effect of clofilium tosylate on the amount of mtDNA in the fibroblasts from a patient with a mutation on each allele of the POLG gene in cell growth conditions cultured in a complete DMEM glucose or galactose medium was measured again. Skin fibroblasts from the control and from the patient were cultured to 100% confluence in a complete DMEM glucose or galactose medium (4.5 g/L of D-glucose or 4.5 g/L of D-galactose, 110 mg/L sodium pyruvate, 10% foetal bovine serum, 1% penicillin/streptomycin from the stock solution containing 10,000 I.U. penicillin and 10,000 μg/mL streptomycin) at 37° C. under 5% $CO_2$. At confluence, the cultures were trypsinised and placed back in culture at 30% confluence in a complete DMEM glucose or galactose medium supplemented with either 0.1% DMSO or with 2.5 μm clofilium tosylate. They were incubated at 37° C. under 5% $CO_2$ and harvested at 100% confluence. The total fibroblast DNAs were extracted by the phenol-chloroform method, and the mtDNA and nuclear DNA were quantified by qPCR as described in Sarzi et al., 2007 (Sarzi, E., Bourdon, A., Chrétien, D., Zarhrate, M., Corcos, J., Slama, A., Cormier-Daire, V., De Lonlay, P., Munnich, A. and Rötig, A. (2007) Mitochondrial DNA Depletion is a Prevalent Cause of Multiple Respiratory Chain Deficiency in Childhood. *J Pediatr,* 105, 531-534).

Example 14: Effect of Clofilium Tosylate on the Amount of mtDNA of the Fibroblasts from a Patient with a Mutation on Each Allele of the POLG Gene, Said Fibroblasts Having been Cultured in Quiescent Conditions Skin fibroblasts from the control and from the patient were cultured to 100% confluence in DMEM at 37° C. under 5% $CO_2$. At 100% confluence, the fibroblasts were washed with PBS and the quiescent medium was added (4.5 g/L D-glucose, 110 mg/L sodium pyruvate, 0.1% foetal bovine serum, 1% penicillin/streptomycin from the stock solution containing 10,000 I.U. penicillin and 10,000 µg/mL streptomycin). After four days in quiescent medium, 1 clofilium tosylate or DMSO (0.1%) was added to the culture medium. The treatment was carried out for 18 days, changing the culture medium with or without clofilium tosylate every three days. The fibroblasts were harvested every 6 days and the total DNA was extracted using phenol-chloroform. The mtDNA and nuclear DNA were quantified by qPCR (Sarzi, E., Bourdon, A., Chrétien, D., Zarhrate, M., Corcos, J., Slama, A., Cormier-Daire, V., De Lonlay, P., Munnich, A. and Rötig, A. (2007) Mitochondrial DNA Depletion is a Prevalent Cause of Multiple Respiratory Chain Deficiency in Childhood. *J Pediatr*, 105, 531-534).

Figure 17:
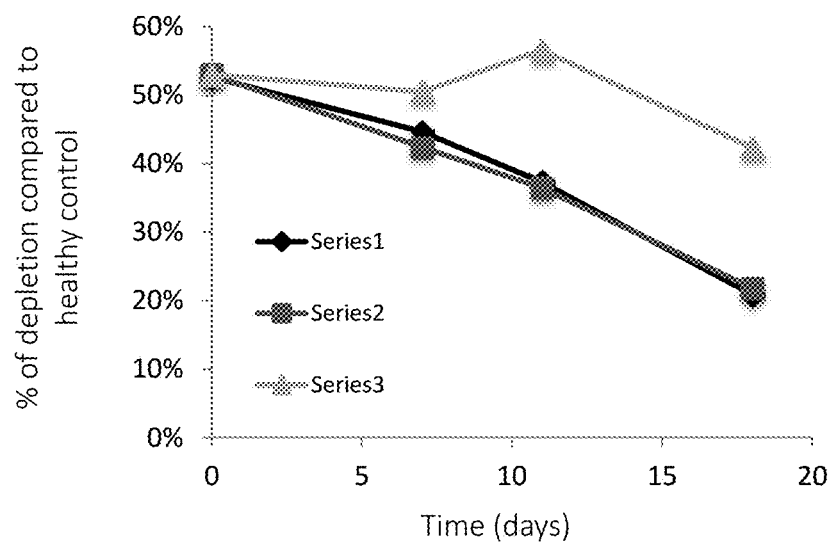
FIG. 17.

The results are shown in FIG. 17.

Clofilium tosylate increased the amount of mtDNA of the fibroblasts from a patient with a mutation on each allele of the POLG gene in quiescent conditions.

The effect of clofilium tosylate on the amount of mtDNA of fibroblasts from a patient with a mutation on each allele of the POLG gene in quiescent conditions was measured a second time in accordance with the same procedure.

Figure 19:
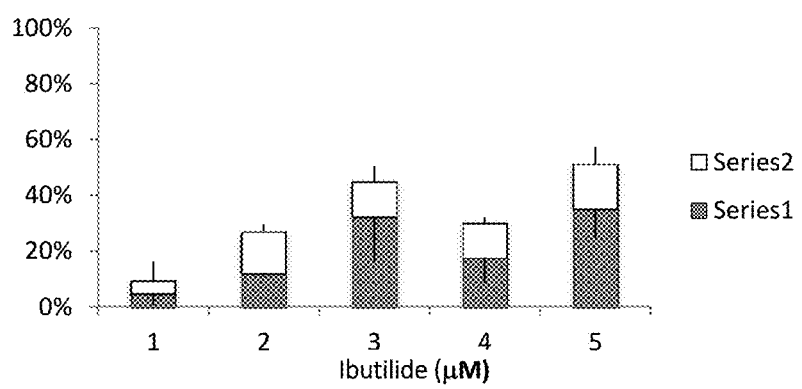
FIG. 19.

Example 15: Dose-response of Ibutilide for the Resistance of Haploinsufficient polg-1(ok1548Δ/+) Nematodes to Ethidium Bromide NGM dishes supplemented with 30 µg/mL ethidium bromide and DMSO or 1 µM, 5 µM, 10 µM or 50 µM ibutilide hemifumarate were prepared (three dishes for each treatment group). Between 30 and 40 larvae of the TB2143 strain (polg-1(ok1548Δ/Δ)) synchronised at stage L1 were deposited on each of these dishes. Their development was observed for 4 days. The results are shown in FIG. 19.

Example 16: Dose-response of Dofetilide for the Resistance of Haploinsufficient polg-1(ok1548Δ/+) Nematodes to Ethidium Bromide NGM dishes supplemented with 30 µg/mL ethidium bromide and DMSO or 1 µM, 5 µM, 10 µM, 50 µM, 100 µM or 200 µM dofetilide or 50 µM clofilium tosylate were prepared (three dishes for each treatment group). Between 30 and 40 larvae of the TB2143 strain (polg-1(ok1548Δ/Δ)) synchronised at stage L1 were deposited on each of these dishes. Their development was observed for 4 days.

Figure 20:
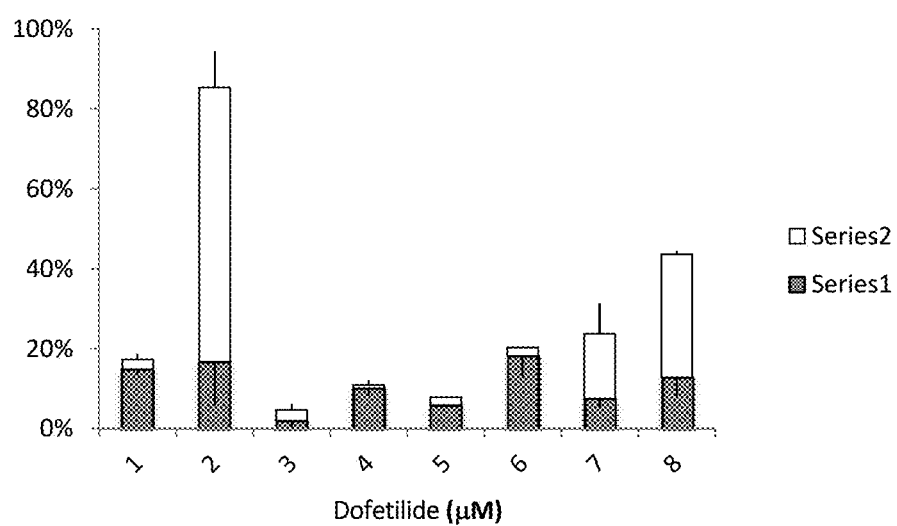
FIG. 20.

The results are shown in FIG. 20.

Example 17: Effect of Clofilium Tosylate on the Production of Small Colonies of the Δfis1 Mutant Yeast Strain The effect of clofilium was evaluated in accordance with the same procedure as for Example 2 with Δfis1 mutant yeasts.

Figure 21:
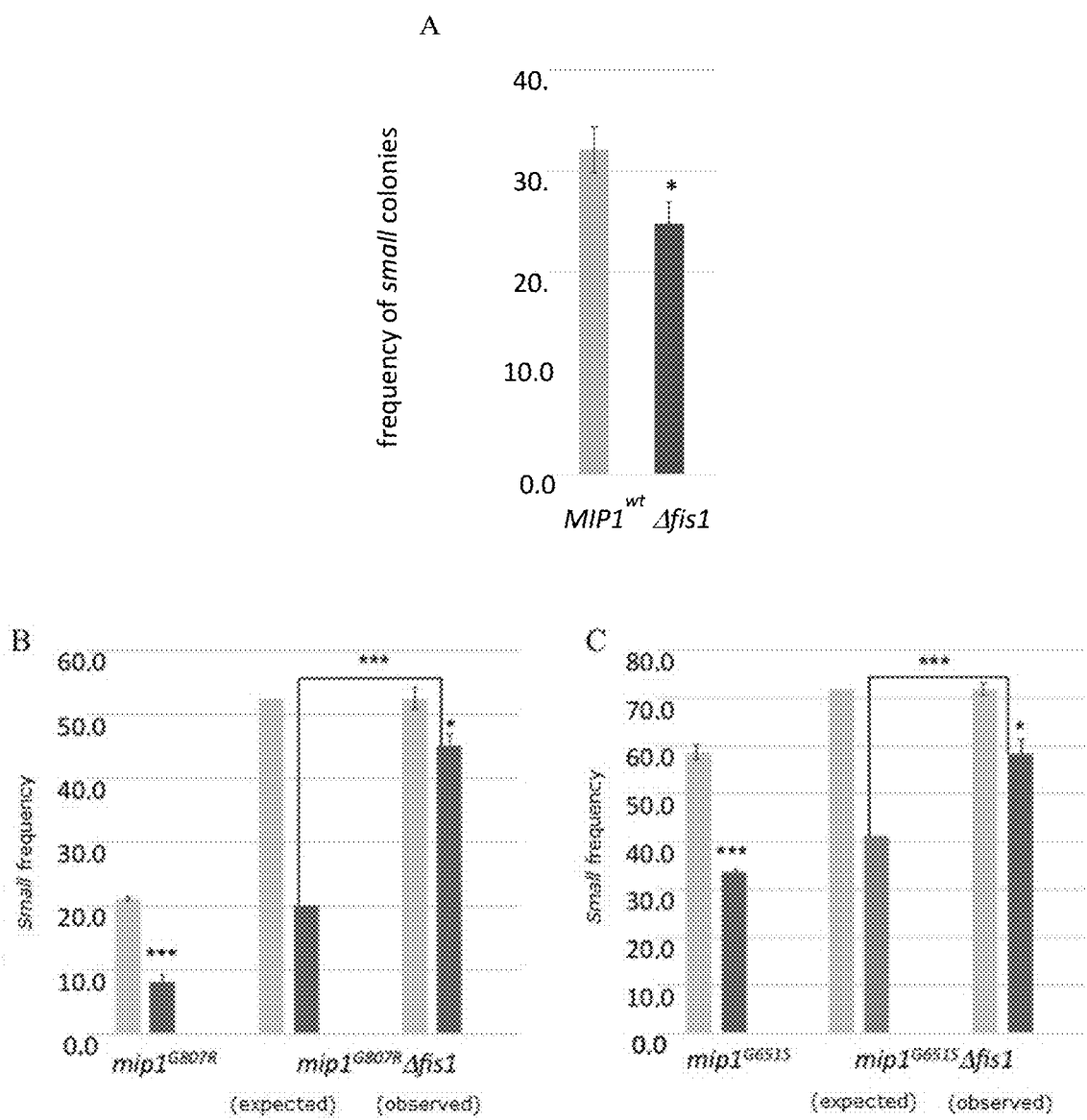
FIG. 21: Part A shows the frequency of the number of small colonies in the presence of 32 clofilium tosylate (dark grey) compared to the frequency of the number of small colonies of untreated cells (DMSO, light grey) in the mutant Δfis1.
Part B shows the frequency of the number of small colonies in the presence of 32 clofilium tosylate (dark grey) compared to the frequency of the number of small colonies of untreated cells (DMSO, light grey) in the mutant $mip1^{G807R}$ as well as the calculated (expected) frequency and that observed in the double mutant $mip1^{G807R}$ Δfis1.
Part C shows the frequency of the number of small colonies in the presence of 32 μM clofilium tosylate (dark grey) compared to the frequency of the number of small colonies of untreated cells (DMSO, light grey) in the mutant $mip1^{G651S}$ as well as the calculated (expected) frequency and that observed in the double mutant $mip1^{G651S}$ Δfis1.

The results are shown in FIG. 21.

The product of the FIS1 gene, which is involved in the process of mitochondrial fission, interferes with the mechanism of action of clofilium tosylate.

Example 18: Broadening of the Dose-response of Clofilium Tosylate for the Amount of mtDNA of Fibroblasts from a Patient with a Mutation on each Allele of the POLG Gene, said Fibroblasts having been Cultured in Quiescent Conditions Skin fibroblasts from the control and from the patient were cultured to 100% confluence in DMEM at 37° C. under 5% $CO_2$. At 100% confluence, the fibroblasts were washed with PBS and the quiescent medium was added (4.5 g/L D-glucose, 110 mg/L sodium pyruvate, 0.1% foetal bovine serum, 1% penicillin/streptomycin from the stock solution containing 10,000 I.U. penicillin and 10,000 µg/mL streptomycin). After four days in quiescent medium, 30 nM, 100 nM, 300 nM or 1 µM clofilium tosylate or DMSO (0.1%) were added to the culture medium. The treatment was carried out for 18 days, changing the culture medium with or without clofilium tosylate every three days. The fibroblasts were harvested every 6 days and the total DNA was extracted using phenol-chloroform. The mtDNA and nuclear DNA were quantified by qPCR (Sarzi, E., Bourdon, A., Chrétien, D., Zarhrate, M., Corcos, J., Slama, A., Cormier-Daire, V., De Lonlay, P., Munnich, A. and Rötig, A. (2007) Mitochondrial DNA Depletion is a Prevalent Cause of Multiple Respiratory Chain Deficiency in Childhood. *J Pediatr*, 105, 531-534).

Example 19: Effect of Clofilium Tosylate on the Amount of mtDNA of Fibroblasts from another Patient with Different Mutations on each Allele of the POLG Gene, said Fibroblasts having been Cultured in Quiescent Conditions Skin fibroblasts from the control and from the patient were cultured to 100% confluence in DMEM at 37° C. under 5% $CO_2$. At 100% confluence, the fibroblasts were washed with PBS and the quiescent medium was added (4.5 g/L D-glucose, 110 mg/L sodium pyruvate, 0.1% foetal bovine serum, 1% penicillin/streptomycin from the stock solution containing 10,000 I.U. penicillin and 10,000 µg/mL streptomycin). After four days in quiescent medium, 1 µM clofilium tosylate or DMSO (0.1%) was added to the culture medium. The treatment was carried out for 18 days, changing the culture medium with or without clofilium tosylate every three days. Fibroblasts were harvested every 6 days and the total DNA was extracted using phenol-chloroform. The mtDNA and nuclear DNA were quantified by qPCR (Sarzi, E., Bourdon, A., Chrétien, D., Zarhrate, M., Corcos, J., Slama, A., Cormier-Daire, V., De Lonlay, P., Munnich, A. and Rötig, A. (2007) Mitochondrial DNA Depletion is a Prevalent Cause of Multiple Respiratory Chain Deficiency in Childhood. *J Pediatr*, 105, 531-534).

Example 20: Effect of Clofilium Tosylate on a Model of Depletion of mtDNA (Not Caused by a Mutation in the POLG Gene) with Mutation in the Orthologous Gene OPA1 (eat-3) in *Caenorhabditis elegans*

20.1. Effect of Clofilium Tosylate on the Phenotypes of the Mutated Homozygous Worm in the Eat-3 gene (Eat-3 (ad426) II; Him-8(e1489) IV): Test for Resistance to Ethidium Bromide Around thirty larvae (wild-type or mutated in eat-3 (DA631 line (eat-3(ad426))) synchronised at stage L1 were deposited on NGM dishes containing different concentrations of ethidium bromide (10, 20, 30, 40, 50 µg/mL) and either DMSO or 50 µM clofilium tosylate (experiment performed in triplicate). Larval development was examined after 4 days of treatment.

20.2. Effect of Clofilium Tosylate on the Number of Laid and Hatched Eggs of DA631 Nematodes and on the Development Thereof Four DA631 larvae (eat-3(ad426)) at stage L4 were deposited on each NGM dish containing either DMSO or 50

µM clofilium tosylate (three dishes for each treatment group). They were incubated at 20° C. to adulthood. The adults were moved every 9 to 12 hours, over 6 to 7 days, to new dishes containing DMSO or 50 µM clofilium tosylate until there were no eggs in the uterus, and the number of laid eggs was counted. Each laying process was monitored in terms of the hatch count and larval development.

20.3. Effect of Clofilium Tosylate on the Amount of mtDNA of DA631 Nematodes

Ten DA361 larvae (eat-3(ad426))—at stage L4 or wild-type—were deposited on each NGM dish containing either DMSO or 50 µM clofilium tosylate (three dishes for each treatment group). They were incubated at 20° C. until the $6^{th}$ day of adulthood. Extraction of the total DNAs of the nematodes was performed with the Nucleospin Kit Tissue kit (Macherey Nagel). The mtDNA and nuclear DNA were quantified as described in Addo et al., 2010 (Addo, M. G., Cossard, R., Pichard, D., Obiri-Danso, K., Rötig, A. and Delahodde, A. (2010) *Caenorhabditis elegans*, a pluricellular model organism to screen new genes involved in mitochondrial genome maintenance. *BBA-Mol. Basis Dis.*, 1802, 765-773).

20.4. Effect of Clofilium Tosylate on the Mitochondrial Morphology of DA631 Nematodes Ten DA361 larvae—at stage L4 or wild-type—expressing GFP addressed to the mitochondria in the muscles of locomotion were deposited on an NGM dish containing either DMSO or 50 µM clofilium tosylate. They were incubated at 20° C. until the $3^{rd}$ day of adulthood. The adults were then anaesthetised and placed between slide and cover slip in order to examine the mitochondrial morphology by fluorescence microscopy.

Example 21: Effect of the Combination of Administration of Resveratrol (Antioxidant) and Clofilium Tosylate on the Fibroblasts from a Patient with a Mutation on each Allele of the POLG Gene 21.1: Effect on Cell Growth Skin fibroblasts from the control and from the patient were cultured in DMEM Galactose (glucose-free DMEM (Life Technologies) supplemented with 10 mM galactose, 10% foetal bovine serum, 200 U/ml penicillin, 200 U/mL streptomycin). Uridine (50 µg/mL) and sodium pyruvate (2.5 mM) were added to the culture medium to maintain the cells expressing a deficiency of the respiratory chain. The cells were incubated in a controlled atmosphere at 37° C. and 5% $CO_2$. Cell growth of patient and control fibroblasts was measured continuously for 140 h using an xCELLigence apparatus (ACEA Biosciences) in 96-well plates. The background noise of the signal was measured with 50 µL of culture medium per well. 50 µL of medium containing 1350 fibroblasts were then added to each well. The impedance measurement was taken every minute for 9 h and then every 15 minutes until the end of the analysis. Clofilium tosylate (≤2 µM) or resveratrol (≤50 µM) or a combination of clofilium tosylate (≤2 µM) and resveratrol (≤50 µM) or DMSO was added from the point of cell seeding. For each drug or combination of drugs and each control, the analysis was performed in triplicate on 96-well plates. A mathematical algorithm made it possible to convert the impedance signal into cell index (CI). This index was proportional to the number of cells adhering to the bottom of the well and their form.

21.2: Effect on the Amount of mtDNA

Skin fibroblasts from the control and from the patient were cultured in DMEM Galactose (glucose-free DMEM (Life Technologies) supplemented with 10 mM galactose, 10% foetal bovine serum, 200 U/mL penicillin, 200 U/mL streptomycin). Uridine (50 µg/mL) and sodium pyruvate (2.5 mM) were added to the culture medium. The cells were incubated in a controlled atmosphere at 37° C. and 5% $CO_2$. At confluence, the cultures were trypsinised and returned to culture at 30% confluence in a full DMEM galactose medium supplemented either with 0.1% DMSO or with clofilium tosylate (≤2 µM), or with resveratrol (≤50 µM), or with a combination of clofilium tosylate (≤2 µM) and resveratrol (≤50 µM). They were incubated at 37° C. under 5% $CO_2$, and were then harvested at 100% confluence. The total DNAs of the fibroblasts were extracted by the phenol-chloroform method, and the mtDNA and nuclear DNA were quantified by qPCR as described in Sarzi et al., 2007 (Sarzi, E., Bourdon, A., Chrétien, D., Zarhrate, M., Corcos, J., Slama, A., Cormier-Daire, V., De Lonlay, P., Munnich, A. and Rötig, A. (2007) Mitochondrial DNA Depletion is a Prevalent Cause of Multiple Respiratory Chain Deficiency in Childhood. *J Pediatr*, 105, 531-534).

Example 22: Effect of Clofilium Tosylate on the Ratio of Complex I/Citrate Synthase Activities and the Lactate Production of Neuronal Cybrids Derived from a MELAS Patient (m.3243A>G tRNA$^{Leu}$ mutation)

The increase in the lactate production is the result of a toxicity of the drug used, but also of a mitochondrial dysfunction (energy deficiency) present in MELAS syndrome.

The activity of the citrate synthase is a marker of mitochondrial mass and makes it possible to standardise the activity of complex I, which is the first enzyme in the mitochondrial respiratory chain and is significantly reduced in MELAS syndrome.

The mutant MELAS neuronal transmitochondrial line, which is the result of the fusion of the immortalised neuoroblastoma parental line SHSY-5Y with fibroblasts carrying the mutation m.3243A>G, was created in the laboratory of Prof. Procaccio.

Neuronal cybrid lines carrying the MELAS mutation and the parental control line were grown in sterile culture flasks and incubated at 37° C. with 5% $CO_2$ in a medium composed of DMEM with 1.5 g/L glucose, 2 mM L-glutamine and supplemented with 10% foetal bovine serum as well as uridine (5 µg/ml) and pyruvate (10 µg/mL). The cells were harvested by trypsinisation in exponential phase and were used for subsequent biochemical or molecular mitochondrial analyses.

The MELAS neuronal cybrid line carrying the mutation seemingly in the homoplasmic state (i.e. reaching almost 100% MELAS mutation) and the SHSY-5Y parental control line were used for measurements of enzyme activities. The neuronal cybrids in culture at confluence of approximately 50% were treated with the vehicle (DMSO) or at a concentration of 300 nM (CT 300 nM) clofilium tosylate. The cells were then incubated at 37° C. under 5% $CO_2$ and harvested after 48 hours of treatment. After trypsinisation, the cybrid cells were centrifuged and frozen in tubes stored at −80° C. in the form of cell pellets. These cell pellets were then analysed by spectrophotometry with measurement of the different mitochondrial biochemical activities, particularly the activity of citrate synthase and the activity of complex I of the respiratory chain. Citrate synthase localised in the mitochondrial matrix catalyses the first reaction in the Krebs cycle. The dosage of its activity is used as an indicator of the amount of mitochondria.

The enzymatic activities of complex I and citrate synthase were measured according to the protocol described in Medjda et al, 2009 (Medja F, Allouche S, Frachon P, Jardel C, Malgat M, Mousson de Camaret B, Slama A, Lunardi J, Mazat J P, Lombès A. Development and implementation of standardized respiratory chain spectrophotometric assays for clinical diagnosis. Mitochondrion. 2009 September; 9(5): 331-9).

The lactate concentration of the culture medium for neuronal cybrid and parental cells was determined by spectrophotometry using an enzymatic kit (Bohringer) on a Hitachi-Roche apparatus (Roche Diagnostics GmbH). Lactate production was measured according to the protocol described in Desquiret et al, 2012 (Desquiret-Dumas V, Gueguen N, Barth M, Chevrollier A, Hancock S, Wallace D C, Amati-Bonneau P, Henrion D, Bonneau D, Reynier P, Procaccio V. Metabolically induced heteroplasmy shifting and L-arginine treatment reduce the energetic defect in a neuronal-like model of MELAS (2012) Biochimica et Biophysica Acta Molecular Basis of Disease. 1822(6):1019-29).

Figure 22:
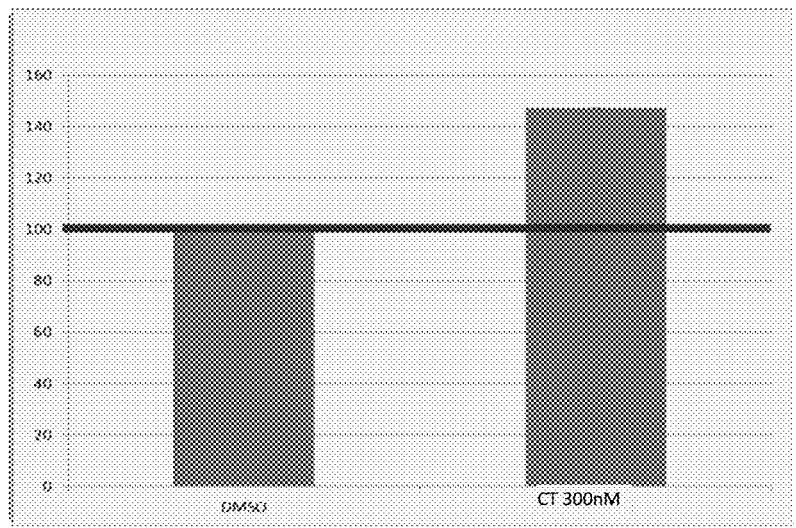
FIG. 22.
Figure 22:
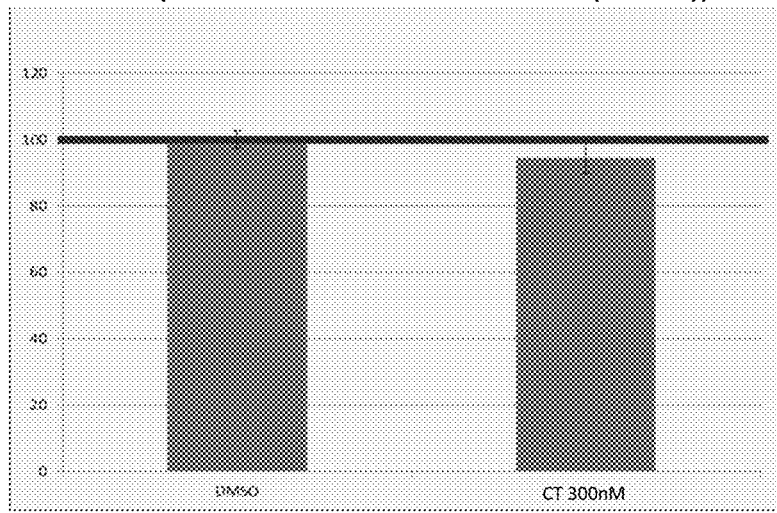

The results are shown in FIG. 22.

Clofilium tosylate increased the activity of complex I without increasing the production of lactate for a cybrid cell line carrying the mutation m.3243A>G for the tRNA$^{Leu}$ responsible for MELAS syndrome.

Example 23: Dose-response of Ibutilide for the Ratio of Complex I/Citrate Synthase Activities and the Lactate Production of Neuronal Cybrids Derived from a MELAS Patient (m.3243A>G tRNA$^{Leu}$ Mutation)

The MELAS neuronal cybrid line carrying the mutation seemingly in the homoplasmic state (i.e. reaching almost 100% MELAS mutation) and the SHSY-5Y parental control line were used for measurements of enzyme activities. The neuronal cybrids in culture at confluence of approximately 50% were treated with the control (DMSO) or at concentrations of 1 µM (ibu 1 µM) or 300 nM (ibu 300 nM) ibutilide. The cells were then incubated at 37° C. under 5% $CO_2$ and harvested after 48 hours of treatment. After trypsinisation, the cybrid cells were centrifuged and frozen in tubes stored at −80° C. in the form of cell pellets. These cell pellets were then analysed by spectrophotometry with measurement of the different biochemical mitochondrial activities, particularly the activity of citrate synthase and the activity of complex I of the respiratory chain. Citrate synthase localised in the mitochondrial matrix catalyses the first reaction in the Krebs cycle. The dosage of its activity is used as an indicator of the amount of mitochondria.

The enzymatic activities were measured according to the protocol described in Medjda et al, 2009 (Medja F, Allouche S, Frachon P, Jardel C, Malgat M, Mousson de Camaret B, Slama A, Lunardi J, Mazat J P, Lombès A. Development and implementation of standardized respiratory chain spectrophotometric assays for clinical diagnosis. Mitochondrion. 2009 September; 9(5):331-9). Lactate production was measured according to the protocol described in Desquiret et al, 2012 (Desquiret-Dumas V, Gueguen N, Barth M, Chevrollier A, Hancock S, Wallace D C, Amati-Bonneau P, Henrion D, Bonneau D, Reynier P, Procaccio V. Metabolically induced heteroplasmy shifting and L-arginine treatment reduce the energetic defect in a neuronal-like model of MELAS (2012) Biochimica et Biophysica Acta Molecular Basis of Disease. 1822(6):1019-29).

Figure 23:
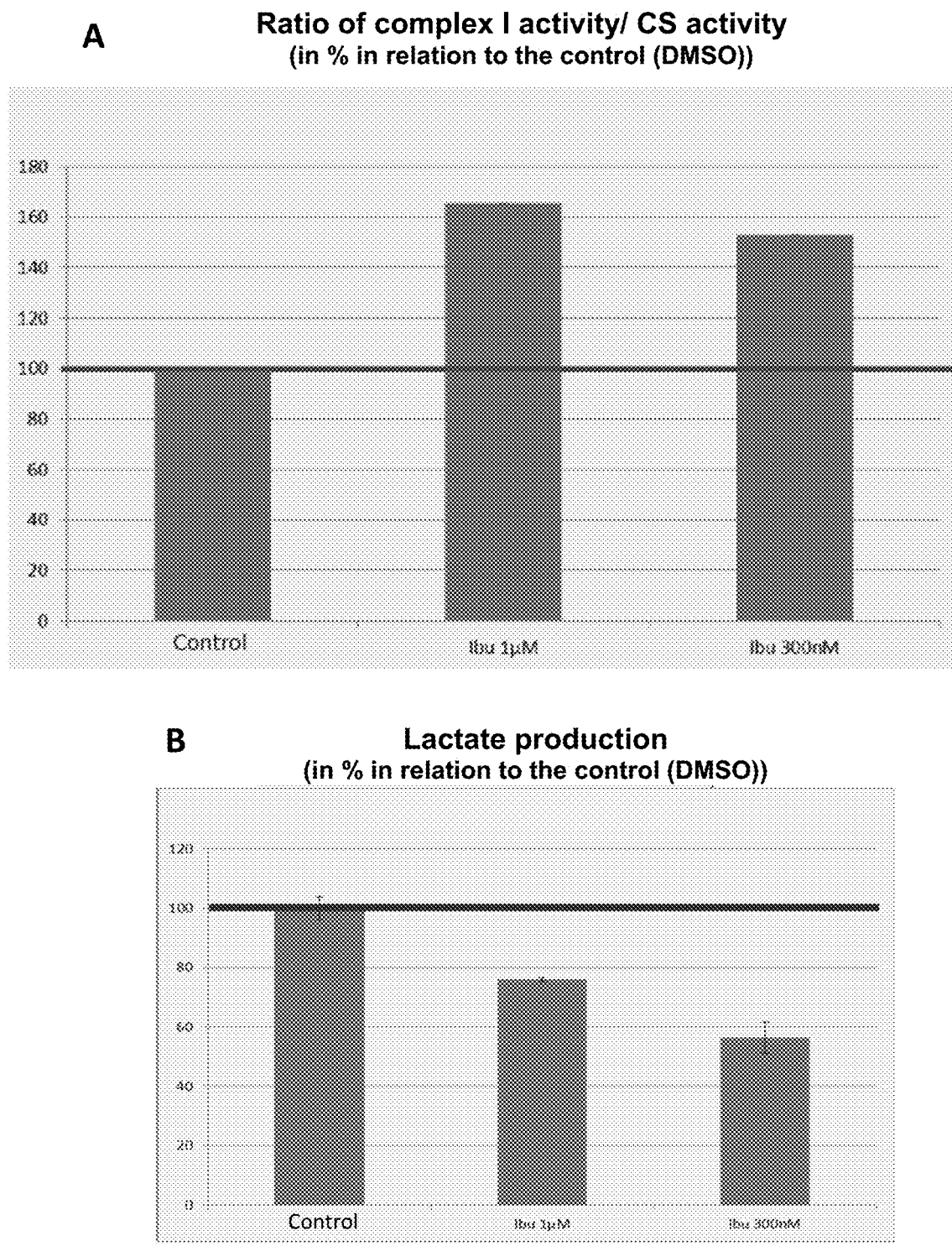
FIG. 23.

The results are shown in FIG. 23.

Ibutilide increased the activity of the complex I and decreased the production of lactate for a cybrid cell line carrying the mutation m.3243A>G for the tRNA$^{leu}$ responsible for MELAS syndrome.

Example 24: Effect of Clofilium Tosylate on the Amount of POLG protein in Control Fibroblasts and in Fibroblasts from a Patient with a Mutation on each Allele of the POLG Gene in Cell Growth Conditions Protein fractions of total extracts of control fibroblasts and of fibroblasts from a patient with a mutation on each allele of the POLG gene cultured in the presence of 0.1% DMSO or with 0.5 µM or 1.0 µM clofilium tosylate were analysed by electrophoresis.

Skin fibroblasts from the control and from the patient were cultured to 100% confluence in a complete Dulbecco's Modified Eagle Medium (DMEM) high glucose medium (4.5 g/L D-glucose, 110 mg/L sodium pyruvate, 10% foetal bovine serum, 1% penicillin/streptomycin from the stock solution containing 10,000 I.U. penicillin and 10,000 µg/mL streptomycin) at 37° C. under 5% $CO_2$. At confluence, the cultures were trypsinised and placed in culture at 30% confluence in a complete DMEM high glucose medium supplemented with either 0.1% DMSO or with 0.5 µM or 1.0 µM clofilium tosylate. The cells were then incubated at 37° C. under 5% $CO_2$ and harvested at 100% confluence. After trypsinisation, the total proteins of the fibroblasts were extracted and analysed by western blot. The proteins studied were the POLG protein (subjected to SDS/PAGE gel analysis (6%)), the mitochondrial proteins ATP5B and TFAM, and the cytosolic protein TUB3A as batch control. 45 µg of proteins were deposited, and, after separation, the proteins were transferred to PVDF membrane and revealed by detecting the peroxidase activity (ECL$^{Plus}$) with the aid of primary antibodies and secondary antibodies coupled to horseradish peroxidase (HRP).

Figure 24:
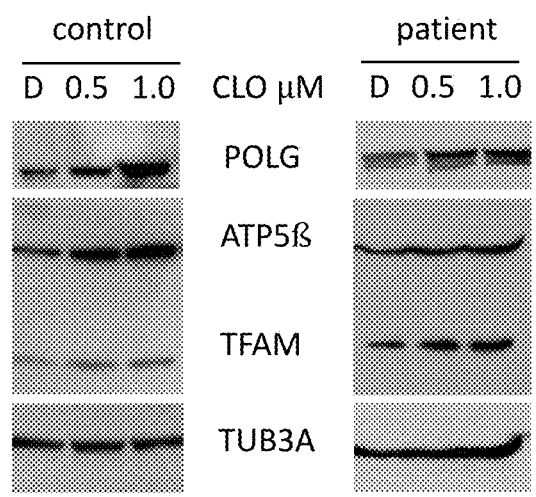
FIG. 24.

The results are shown in FIG. 24.

Clofilium tosylate increased the amount of mitochondrial proteins POLG, TFAM and ATP5B.

Example 25: Dose-response of Clofilium Tosylate for the Amount of mtDNA of the Fibroblasts from a Patient with a Mutation on Each Allele of the POLG Gene, Said Fibroblasts Having Been Cultured in Quiescent Conditions Skin fibroblasts from the patient were cultured to 100% confluence in DMEM at 37° C. under 5% $CO_2$. At 100% confluence, the fibroblasts were washed in PBS and the quiescent medium was added (4.5 g/L D-glucose, 110 mg/L sodium pyruvate, 10% foetal bovine serum, 1% penicillin/streptomycin from the stock solution containing 10,000 I.U. penicillin and 10,000 µg/mL streptomycin). After four days in quiescent medium, clofilium tosylate in an amount of 0.5 µM, 1 µM, 2.5 µM or DMSO (0.1%) were added to the culture medium. The treatment was performed over 18 days, changing the culture medium with or without clofilium tosylate every three days. The fibroblasts were harvested every 6 days, and total DNA was extracted using phenol-chloroform. The mtDNA and nuclear DNA were quantified by qPCR (Sarzi, E., Bourdon, A., Chrétien, D., Zarhrate, M., Corcos, J., Slama, A., Cormier-Daire, V., De Lonlay, P., Munnich, A. and Rötig, A. (2007) Mitochondrial DNA Depletion is a Prevalent Cause of Multiple Respiratory Chain Deficiency in Childhood. *J Pediatr*, 105, 531-534).

Figure 25:
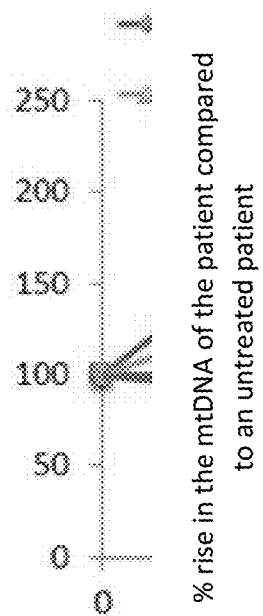
FIG. 25.

The results are shown in FIG. 25.

Clofilium tosylate increased the amount of mtDNA of the fibroblasts from a patient with a mutation on each allele of the POLG gene in quiescent conditions for concentrations of clofilium tosylate of 0.5 µM and 1 µM.

The invention claimed is:

1. Method for the treatment of diseases relating to the instability of mitochondrial DNA comprising administering to a patient having instability of mitochondrial DNA a compound of formula Ia:

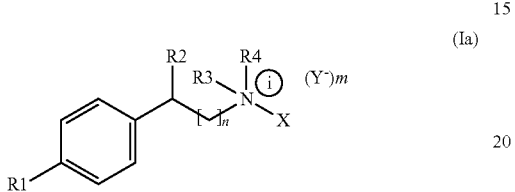

in which
$R_1$ represents a halogen atom, in particular Cl or Br, a C1-C4 alkoxy group, a C1-C3 alkyl group, or $NHSO_2R_6$;
$R_2$ represents OH or H;
$R_3$ and $R_4$ independently of one another represent an alkyl group having 1 to 10 carbon atoms or

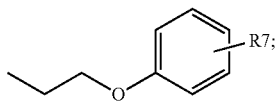

in which $R_7$ represents a hydrogen atom, a halogen atom, a C1-C4 alkoxy group, a C1-C3 alkyl group, or $NHSO_2R_8$;
$R_6$ and $R_8$ independently of one another represent a C1-C4 alkyl group;
—X═—$R_5$ or the non-bonded electron pair of nitrogen, on the condition that i=+ when —X═—$R_5$;
$R_5$ represents a hydrogen atom or a C1-C4 alkyl group;
m=0 or 1, on the condition that m=1 when —X═—$R_5$ and m=0 when —X═ the non-bonded electron pair of nitrogen;
n=0, 1, 2 or 3;
$Y^-$ is a therapeutically acceptable anion, in particular $Y^-$ is selected from the tosylate ion, the carbonate ion, the phosphate ion, and the chloride ion.

2. Method according to claim 1 wherein the compound is of formula Ia:

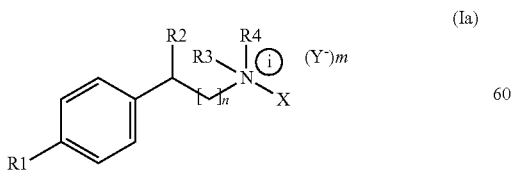

in which
$R_1$ represents Cl, Br, or $NHSO_2R_6$;
$R_2$ represents OH or H;
$R_3$ and $R_4$ independently of one another represent an alkyl group

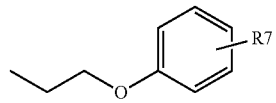

having 1 to 10 carbon atoms or
where $R_7$ represents a halogen atom or $NHSO_2R_8$, on the condition that $R_3$ and $R_4$ cannot simultaneously be

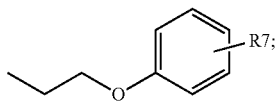

$R_6$ and $R_8$ independently of one another represent a C1-C4 alkyl group;
—X═—$R_5$ or the non-bonded electron pair of nitrogen, on the condition that i=+ when —X═—$R_5$;
$R_5$ represents a C1-C4 alkyl group;
m=0 or 1, on the condition that m=1 when —X═—$R_5$ and m=0 when —X═the non-bonded electron pair of nitrogen;
n=0, 1, 2 or 3;
$Y^-$ is selected from the tosylate ion, the carbonate ion, the phosphate ion and the chloride ion.

3. Method according to claim 1, wherein the compound is of formula Iaa:

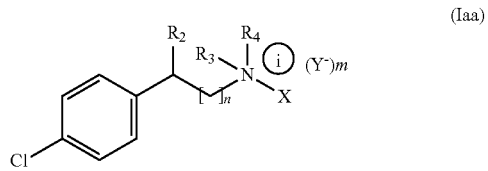

or of formula Iab:

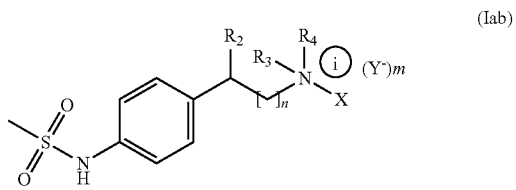

in which R2, R3, R4, —X, R5,

$Y^-$, m and n have the meanings indicated in claim 1.

4. Method according to claim 1, wherein the compound is of formula (a):

(a)
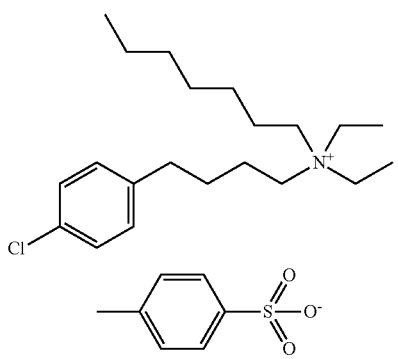
or of formula (b):
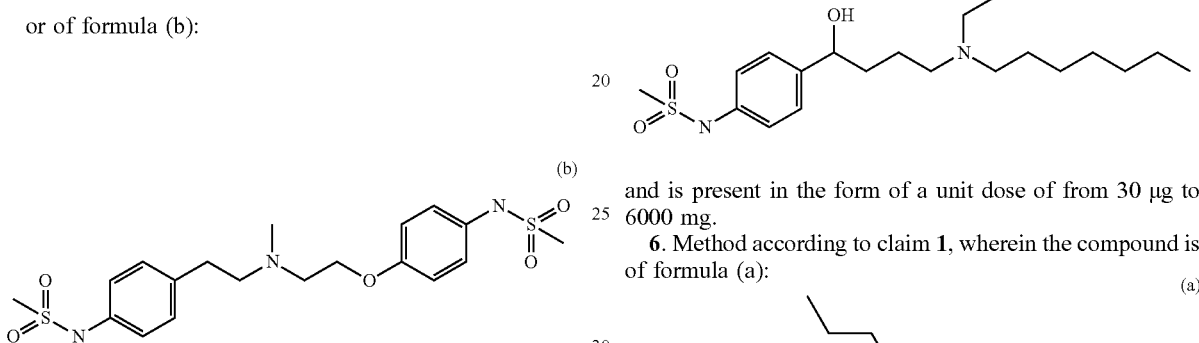
or of formula (c):
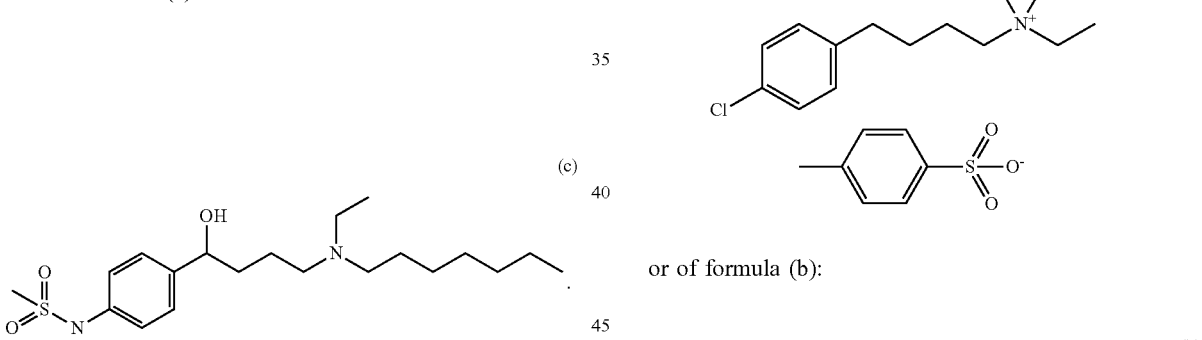
5. Method according to claim 1, wherein the compound is of formula (a):
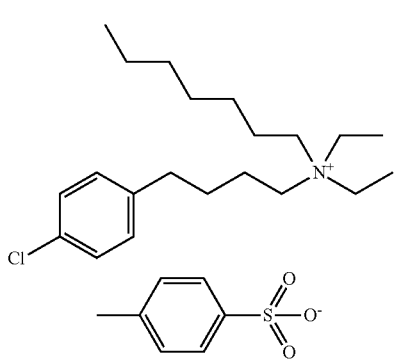
or of formula (b):
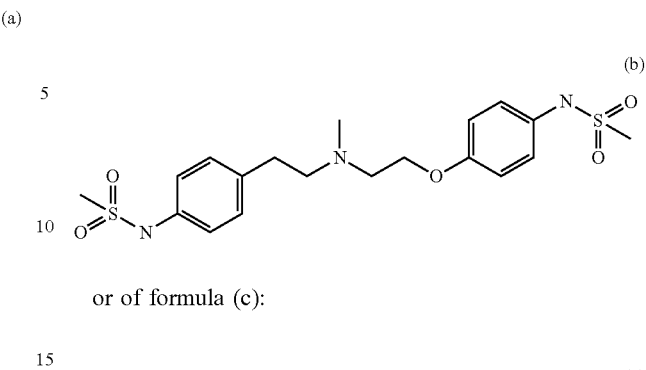
or of formula (c):
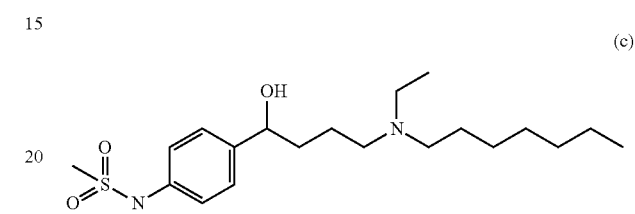
and is present in the form of a unit dose of from 30 μg to 6000 mg.
6. Method according to claim 1, wherein the compound is of formula (a):
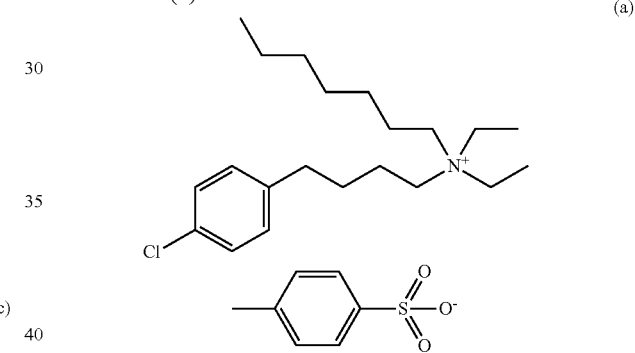
or of formula (b):
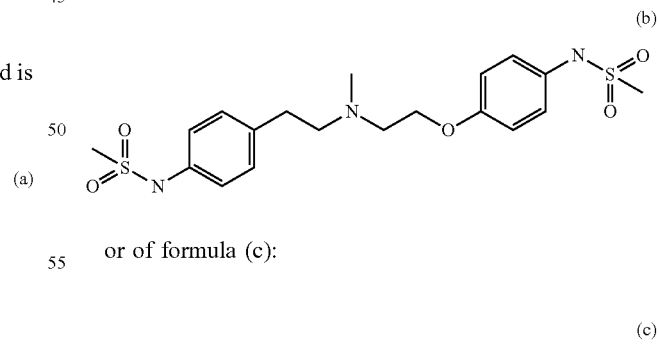
or of formula (c):
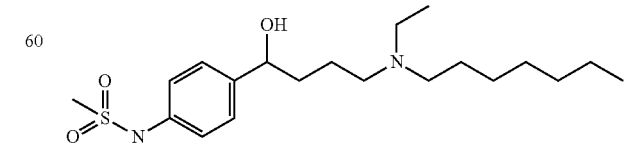
and is present in the form of a unit dose of from 30 μg to 6000 mg, for oral administration, or is present in the form of a unit dose of from 30 µg to 6000 mg, for intravenous administration.

7. Method according to claim 1, wherein the compound is of formula (a):

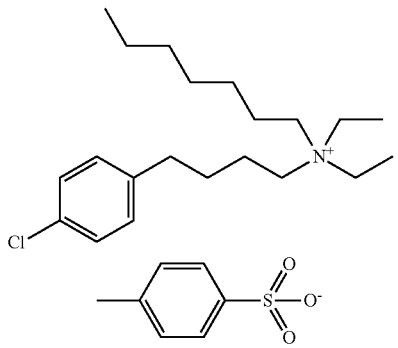

(a)

and is present in the form of a unit dose of from 1.5 mg to 60 mg for oral administration, or present in the form of a unit dose of from 0.5 mg to 30 mg, for intravenous administration.

8. Method according to claim 1, wherein the compound is of formula (b):

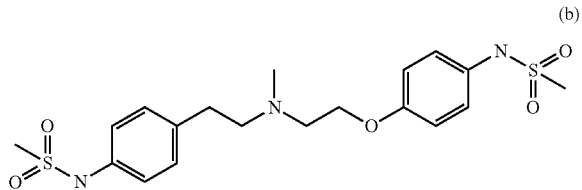 [SMILES: CN(CCOc1ccc(NS(C)(=O)=O)cc1)CCc1ccc(NS(C)(=O)=O)cc1]

(b)

and is present in the form of a unit dose of from 125 to 500 µg, for oral administration.

9. Method according to claim 1, wherein the compound is of formula (c):

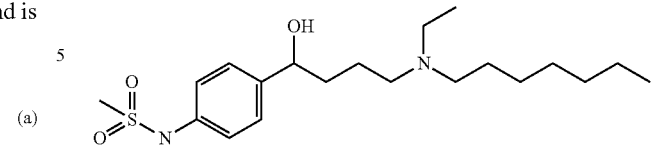

(c)

and is present in the form of a unit dose of from 150 to 2500 µg, for intravenous administration.

10. Method according to claim 1, for the treatment of diseases relating to at least one mutation, or at least one deletion or at least one insertion, or a combination thereof, in the POLG gene, or of diseases relating to the instability of mitochondrial DNA not associated with mutations of the POLG gene, or of diseases associated with a depletion or a deletion of mitochondrial DNA, or of diseases associated with a point mutation of mitochondrial DNA.

11. Method according to claim 1, for the treatment
of diseases associated with quantitative or qualitative abnormalities of mitochondrial DNA, such as Alpers disease (AHS), childhood myocerebrohepatopathy spectrum (MCHS), myoclonic epilepsy myopathy sensory ataxia (MEMSA), spinocerebellar ataxia with epilepsy (SCAE), ataxia with neuropathy syndromes including MIRAS and SANDO, autosomal recessive progressive external ophthalmoplegia (arPEO), autosomal dominant progressive external ophthalmoplegia (adPEO), mitochondrial neurogastrointestinal encephalopathy (MNGIE), Pearson syndrome, Kearns-Sayre syndrome, infantile myopathy and spinal muscular atrophy relating to TK2 mutations, liver failure with depletion of mtDNA, pathologies associated with mutations of the genes SUCLA2 and SUCLAG1, RRM2B, AIF1, MPV17, or
of diseases associated with point mutations of mitochondrial DNA, such as Leber hereditary optic neuropathy, MELAS syndrome, MERRF syndrome, and some forms of Leigh syndrome, chronic progressive external ophthalmoplegia, myopathy, cardiomyopathy, diabetes-deafness, encephalomyopathy, and deafness.

12. Method according to claim 1, for the treatment of MELAS syndrome.

* * * * *